US008445670B2

(12) United States Patent (10) Patent No.: US 8,445,670 B2
Moriarty et al. (45) Date of Patent: May 21, 2013

(54) COMBINATORIAL LIBRARY APPROACH TO IMINOCYCLITOLS WITH BIOLOGICAL ACTIVITY

(75) Inventors: Robert M. Moriarty, Chicago, IL (US); Carmen Mitan, Bucuresti (RO); Kenneth R. Phares, Chapel Hill, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

(21) Appl. No.: 12/382,460

(22) Filed: Mar. 17, 2009

(65) Prior Publication Data

US 2009/0182154 A1 Jul. 16, 2009

Related U.S. Application Data

(62) Division of application No. 11/514,339, filed on Sep. 1, 2006.

(60) Provisional application No. 60/713,344, filed on Sep. 2, 2005.

(51) Int. Cl.
*C08B 37/00* (2006.01)
*C07H 5/04* (2006.01)
*C07H 5/06* (2006.01)

(52) U.S. Cl.
USPC ........................................................ 536/55.3

(58) Field of Classification Search
None
See application file for complete search history.

(56) References Cited

U.S. PATENT DOCUMENTS

| 5,229,523 | A | 7/1993 | Wong et al. |
| 5,276,120 | A | 1/1994 | Wong et al. |
| 5,461,143 | A | 10/1995 | Wong et al. |
| 5,579,823 | A | 12/1996 | Mikol et al. |
| 5,596,005 | A | 1/1997 | Wong et al. |
| 6,232,450 | B1 | 5/2001 | Wong |
| 6,462,193 | B1 | 10/2002 | Wong et al. |
| 6,774,140 | B1 | 8/2004 | Wong et al. |
| 2004/0147591 | A1 | 7/2004 | Kanie et al. |
| 2007/0088164 | A1 | 4/2007 | Moriarity et al. |

FOREIGN PATENT DOCUMENTS

WO  WO 2005/070418 A1  8/2005

OTHER PUBLICATIONS

Yang et al. J. Org. Chem. 2002, 67, 3773-3782.*
Cipolla et al. Current Topics in Medicinal Chemistry 2003, 3, 485-511.*
Rajeskhar et al. Carbohydrate Research 338 (2003) 801-805.*
Deferrari et al. Journal of Organic Chemistry, 1959, vol. 24, pp. 183-186.*
Al Daher et al., "Change in specificity of glycosidase inhibition by N-alkylation of amino sugars," Biochem. J., 1989, 258(2), 613-615.
Asano et al., "Sugar-mimic glycosidase inhibitors: natural occurrence, biological activity and prospects for therapeutic application," Tetrahedron: Asymmetry 2000, 11, 1645-1680.
Asano et al., "Glycosidase inhibitors: update and perspectives on practical use," Glycobiology, 2003, 13(10), 93R-104R.
Baldwin et al., "Rules for Ring Closure," J. Chem. Soc. Chem. Commun., 1976, 18, 734-736.
Block et al., "Secretion of human hepatitis B virus is inhibited by the imino sugar N-butyldeoxynojirimycin," Proc. Natl. Acad. Sci. U. S. A. Mar. 1994, 91(6), 2235-2239.
Bols, M. "1-Aza sugars, Apparent Transition State Analogues of Equatorial Glycoside Formation/Cleavage," Acc. Chem. Res. 1998, 31, 1-8.
Boucheron et al., "Design and synthesis of iminosugar-based inhibitors of glucosylceramide synthase: the search for new therapeutic agents against Gaucher disease," Tetrahedron: Asymmetry, 2005, 16(10), 1747-1756.
Branza-Nichita et al., "Antiviral Effect of N-Butyldeoxynojirimycin against Bovine Viral Diarrhea Virus Correlates with Misfolding of E2 Envelope Proteins and Impairment of Their Association into E1-E1 Heterodimers," J Virol. 2001, 75(8), 3527-3536.
Butters et al., "Amino sugar inhibitors for treating the lysosomal glycosphingolipidoses," Glycobiology, 2005, 15(10), 43R-52R.
Cenci di Bello et al., "Structure-activity relationship of swainsonine," Biochem. J., 1989, 259(3), 855-861.
Chapman et al., "Glyco- and Peptidomimetics from Three-Component Joullie-Ugi Coupling Show Selective Antiviral Activity," J. Am. Chem. Soc. 2005, 127, 506-507.
Cipolla et al., "Synthesis of Azasugars by Grignard Reaction on Glycosylamines," Tetrahedron, 1995, 51(16), 4679-4690.
Cook et al., "Species Dependent Esterase Activities for Hydrolysis of an Anti-HIV Prodrug Glycovir and Bioavailability of Active SC-48334," Pharmaceutical Research 1995, 12(8), 1158-1164.
Duff et al., "Synthesis of aza-C-disaccharides using cycloaddition reactions of a functionalized cyclic nitrone," Chem. Commun. 2000, 2127-2128.
Durantel et al., "Effects of Interferon, Ribavirin, and Iminosugar Derivatives on Cells Persistently Infected with noncytopathic Bovine Viral Diarrhea Virus," Antimicrob. Agents and Chemother., 2004, 48(2), 497-504.
Durantel et al., "Study of the Mechanism of Antiviral Action of Iminosugar Derivatives against Bovine Viral Diarrhea Virus," J Virol. 2001, 75(19), 8987-8998.
Evans et al., "Synthesis of Transition State Analogue Inhibitors for Purine Nucleoside Phosphorylase and N-Riboside Hydrolases," Tetrahedron 2000, 56, 3053-3062.

(Continued)

*Primary Examiner* — Layla Bland
(74) *Attorney, Agent, or Firm* — Foley & Lardner LLP

(57) ABSTRACT

A method of synthesizing stereochemically defined iminocyclitol comprises replacing an intraring oxygen in a cyclic sugar by an intraring imine to form an iminocyclitol, wherein said iminocyclitol has a defined stereochemical configuration different from a stereochemical configuration of the cyclic sugar. The invention also provides combinatorial libraries of iminocyclitol compounds, allowing for diverse C1 and N-substitution. In addition, provided are methods of treating viral infections with iminocyclitols compounds.

36 Claims, 14 Drawing Sheets

OTHER PUBLICATIONS

Evans et al., "Addition of Lithiated 9-Deazapurine Derivatives to a Carbohydrate Cyclic Imine: Convergent Synthesis of the Aza-C-nucleoside Immucillins," J. Org. Chem. 2001, 66, 5723-5730.

Fleet et al., "Practical synthesis of deoxymannojirimycin and mannonolactam from L-gulonolactone. Synthesis of L-deoxymannojirimycin and L-mannonolactam from D-gulonolactone," Tetrahedron 1989, 45(1), 319-326.

Fleet et al., "Short synthesis of D-deoxymannojirimycin and D-mannonolactam from L-gulonolactone and of L-deoxymannojirimycin and L-mannonolactam from D-gulonolactone," Tetrahedron Letters 1988, 29(23), 2871-2874.

Fleet et al., "Short Efficient Synthesis of the α-L-Fucosidase Inhibitor, Deoxyfuconojirimycin [1,5-Dideoxy-1,5-imino-L-fucitol]from D-Lyxonolactone," J. Chem. Soc. Perkin Trans 1, 1989, 665-666.

Furneaux et al., "Synthesis of Transition State Inhibitors for N-Riboside Hydrolases and Transferases," Tetrahedron 1997, 53, 2915-2930.

Ganem, B., "Inhibitors of Carbohydrate-Processing Enzymes: Design and Synthesis of Sugar-Shaped Heterocycles," Acc. Chem. Res 1996, 29, 340-347.

Godseken et al., "Deoxyiminoalditols from Aldonolactones—V. Preparation of the Four Stereoisomers of 1,5-Dideoxy-1,5-iminopentitols. Evaluation of these Iminopentitols and Three 1,5-Dideoxy-1,5-iminoheptitols as Glycosidase Inhibitors," Bioorg. Med. Chem., 1996, 4(11), 1857-1865.

Gogskesen et al., "Unusual ring contraction by substitution of 4-O-activated-pentono-1,5-lactams with cyanide. Stereospecific synthesis of 6-amino-1,4,5,6-tetradeoxy-1,4-imino-hexitols," Tetrahedron: Asymmetry 2000, 11, 567-579.

Goodyear et al., "The Oxide-ring Structure of Normal and γ-Derivates of Mannose . . . " J. Chem. Soc. 1927, 3136-3146.

Han et al., "Spectroscopic, Crystallographic and Computational Studies of the Formation and Isomerization of Cyclic Acetals and ketals of Pentonolactones," Tetrahedron: Asymmetry 1997, 5(12), 2535-2562.

Han et al., "Mannich-Type C-Nucleosidations with 7-Carba-purines and 4-Aminopyrimjidines," Synlett 2005, 5, 744-750.

Heightman et al., "Recent Insights into Inhibition, Structure, and Mechanism of Configuration-Retaining Glycosidases," Angew. Chem. Int. Ed. Engl. 1999, 38, 750-770.

Horenstein et al., "A New Class of C-Nucleoside Analogues. 1-(S)-aryl-1,4-dideoxy-1,4-imino-D-ribitols, Transition State Analogue Inhibitors of Nucleoside Hydrolase," Tetrahedron Lett. 1993, 34(45), 7213-7216.

Joseph et al., "Syntheses of (3R,4R,5R,6R)-tetrahydroxyazepane (1,6-dideoxy-1,6-imino-D-mannitol) and (3S, 4R, 5R, 6F)-tetrahydroxyazepane (1,6-dideoxy-1,6-imino-D-glucitol)," Tetrahedron 2002, 58, 6907-6911.

Karpas et al., "Aminosugar derivatives as potential anti-human immunodeficiency virus agents," PNAS US 1988, 85(23), 9229-9233.

Legler, G. "Glycoside hydrolases: Mechanistic Information from studies with reversible and irreversible inhibitors," Adv. Carbohydr. Chem. Biochem. 1990, 48, 319-385.

Look et al., "Enzyme-Catalyzed Organic Synthesis: Practical Routes to Aza Sugars and Their Analogs for Use as Glycoprocessing Inhibitors," Acc. Chem. Res 1993, 26, 182-190.

Lu et al., "Aberrant trafficking of hepatitis B virus glycoproteins in cells in which N-glycan processing is inhibited," PNAS USA 1997, 94(6) 2380-2385.

Lu et al., "Evidence that N-linked glycosylation is necessary for hepatitis B virus secretion," Virology, 1995, 213(2), 660-665.

Lu et al., "The Alkylated Imino Sugar, n-(n-Nonyl)-Deoxygalactonojirimycin, Reduces the Amount of Hepatitis B Virus Nucleocapsid in Tissue Culture," J. Virol. 2003, 77(22), 11933-11940.

Lundt et al., "Deoxyiminoalditols from Aldonolactones. III. Preparation of 1,4-Dideoxy-1,4-imino-L-gulitol.—Evaluation of 1,4-Dideoxy-1,4-iminohexitols as Glycosidase Inhibitors," Tetrahedron, 1994, 50(25), 7513-7520.

Manna et al., "2,3,4-Tri-O-acetyl-1,6-anhydro-β-D-mannopyranose, an artifact produced during carbohydrate analysis. A total synthesis of 2,3,5-tri-O-acetyl-1,6-anhydro-β-D-mannofuranose," Carbohydr. Res. 1993, 243, 11-27.

Mehta et al., "β-Galactosylceramide and Novel Synthetic Glycolipids Directly Induce the Innate Host Defense Pathway and Have Direct Activity against Hepatitis B and C Viruses," Antimicrob. Agents. Chemother., 2004, 48(6), 2085-2090.

Mehta et al., "Inhibition of Hepatitis B Virus DNA Replication by Imino sugars Without the Inhibition of the DNA Polymerase: Therapeutic Implications," Hepatology, 2001, 33(6), 1488-1495.

Mehta et al., "Structure-Activity Relationship of a New Class of Anti-Hepatitis B Virus Agents,"Antimicrob. Agents and Chemother. 2002, 46(12), 4004-4008.

Mehta et al., "Imino sugars that are less toxic but more potent as antivirals, in vitro, compared with N-n-nonyl DNJ," Antivir. Chem. Chemother. 2002, 13(5), 299-304.

Mellor et al., "Preparation, biochemical characterization and biological properties of radiolabelled N-alkylated deoxynojirimycins," Biochem. J., 2002, 366, 225-233.

Moriarty et al., "exo-Imino to endo-Iminocyclitol Rearrangement. A General Route to Five-membered Antiviral Azasugars," Org. Lett., 2006, 8(16) 3465-3467.

O Hagan, D., "Pyrrole, pyrrolidine, pyridine, piperidine, azepine and tropane alkaloids," Nat. Prod. Rep. 1997, 14, 637-651.

Ogura et al., "Reaction of Ethynyl Compounds with Lactones," J. Org. Chem. 1972, 37, 72-75.

Ohle H.; Berend G. Chem. Ber. 1925, 58, 2590-2592.

Pearson et al., "Recent Advances in the total Synthesis of Piperidine Azasugars," Eur. J. Org. Chem. 2005, 2159-2191.

Saotome et al., "Combinatorial library of five-membered iminocyclitol and the inhibitory activities against glycol-enzymes," Chemistry & Biology, 2001, 8, 1061-1070.

Sifferlen et al., "Chiral 5-Methyl-trihydroxypyrrolidines-Preparation from 1,2-Oxazines and Glycosidase Inhibitory Properties," Tetrahedron, 2000, 56, 971-978.

Sletten et al., "A Flexible Stereospecific Synthesis of Polyhydroxylated Pyrrolizidines from Commercially Available Pyranosides," J. Org. Chem., 2006, 71, 1335-1343.

Stütz, A. E., "8: Some Reflections on Structure-Activity Relationships in Glycosidase-Inhibiting lminoalditols and Iminosugars," Iminosugars as Glycosidase Inhibitors: Nojirimycin and Beyond; Ed. Wiley-VCH: Weinheim, 1999, 157-187.

Stütz, A. E., "A Novel Approach for Clarifying the Reaction Mechanism of Retaining Glycoside Hydrolases," Angew. Chem. Int. Ed. Engl. 1996, 35, 1926-1928.

Tam et al., "Chiral Models of the Furenone Moiety of Germacranolid Sesquiterpenes," J. Org. Chem., 1980, 45, 1344-1346.

Tenud et al., "Endocyclishce $S_N$-Reaktionen am gesattigten Kohlenstoff?," Helv. Chim. Acta, 1970, 53(8), 2059-2069.

Ting et al., "Targeting a Novel *Plasmodium falciparum* Purine Recycling Pathway with Specific Immucillins," J. Biol. Chem. 2005, 280(10), 9547-9554.

Tuchscherer et al., "The Tasp Concept: Mimetics of peptide ligands, protein surfaces and folding units," Tetrahedron, 1993, 49(16), 3359-3575.

Vonlanthen et al., "Hydroxycyclopentanone Derivatives from D-Mannose via Ring Closing Metathesis: An Improved Synthesis of a Key Intermediate of Tricyclo-DNA," Synthesis 2003, 7, 1087-90.

Wang et al., "Chemo-enzymatic Synthesis of Five-membered Azasugars as Inhibitors of Fucosidase and Fucosyltransferase: An Issue Regarding the Stereochemistry Discrimination at Transition States," Tetrahedron Lett., 1993, 34(3), 403-406.

Wang et al., "Synthesis and Biological Evaluation of Glycosidase Inhibitors: *gem*-Difluoromethylenated Nojirimycin Analogues," J. Med. Chem., 2006, 49, 2989-2997.

Winchester et al., "Amino-sugar glycosidase inhibitors: versatile tools for glycobiologists," Glycobiology 1992, 2, 199-210.

Zitzmann et al., "Imino sugars inhibit the formation and secretion of bovine viral diarrhea virus, a pestivirus model of hepatitis C virus: Implications for the development of broad spectrum anti-hepatitis virus agents," Proc. Natl. Acad. Sci. USA, 1999, 96(21), 11878-11882.

Altan et al, "Defective Acidification in Human Breast Tumor Cells and Implications for Chemotherapy," J. Exp. Med., May 18, 1998, 187(10):1583-1598.

Branza-Nichita et al., "Mutations at Critical N-Glycosylation Sites Reduce Tyrosinase Activity by Altering Folding and Quality Control," J. Biol. Chem., Mar. 17, 2000, 275(11):8169-8175.

Cao et al., "Biochemotherapy with temozolomide, cisplatin, vinblastine, subcutaneous interleukin-2 and interferon-αin patients with metastatic melanoma," Melanoma Research, 2006, 16(1):59-64.

Chapman et al., "Phase III Multicenter Randomized Trial of the Dartmouth Regimen Vresus Dacabazine in Patients with Metastatic Melanoma," J. Clinical Oncology, Sep. 1999, 17(9):2745-2751.

Chintala et al., "Induction of Matrix Metalloproteinase-9 Requires a Polymerized Actin Cytoskeleton in Human Malignant Glioma Cells," J. Biol. Chem., May 29, 1998, 273(22):13545-13551.

Cuervo, Ana Maria, "Autophagy: in sickness and in health," Trends in Cell Biology, Feb. 2004, 14(2):70-77.

Daido et al., "Pivotal Role of the Cell Death Factor BNIP3 in Ceramide-Induced Autophagic Cell Death In Malignant Glioma Cells," Cancer Research, Jun. 15, 2004, 64:4286-4293.

Del Prete et al., "Combination Chemotherapy with Cisplatin, Carmustine, Dacarbazine and Tamoxifen in Metastatic Melanoma," Cancer Treatment Reports, Nov. 1984, 68(11):1403-1405.

Gijsbers et al., "GCP-2/CXCL6 synergizes with other endothelial cell-derived chemokines in neutrophil mobilization and is associated with angiogenesis in gastrointestinal tumors," Experimental Cell Research, 2005, 303:331-342.

Gozuacik et al., "Autophagy as a cell death and tumor suppressor mechanism," Oncogene, 2004, 23:2891-2906.

Grossman et al., "Drug resistance in melanoma: Mechanisms, apoptosis, and new potential therapeutic targets," Cancer and Metastasis Reviews, 2001, 20:3-11.

Guerrera et al., "N-butyldeoxynojirimycin inhibits murine melanoma cell ganglioside metabolism and delays tumor onset," Medline, Jan. 1, 1900, XP003007567, 1 page (abstract of Cancer Letters, Ireland, Nov. 10, 2003, vol. 201).

International Search Report and Written Opinion mailed Jun. 15, 2009 in PCT/US2008/060822, 19 pages.

Kabeya et al., "LC3, a mammalian homologue of yeast Apg8p, is localized in autophagosome membranes after processing," The EMBO Journal, 2000, 19(21):5720-5728.

Kanzawa et al., "Induction of Autophagic Cell Death in Malignant Glioma Cells by Arsenic Trioxide," Cancer Research, May 1, 2003, 63:2103-2108.

Kanzawa et al., "Role of autophagy in temozolomide-induced cytotoxicity for malignant glioma cells," Cell Death and Differentiation, 2004, 11:448-457.

Khayat et al., "Fotemustine in the Treatment of Brain Primary Tumors and Metastases," Cancer Investigation, 1994, 12(4):414-420.

Klionsky et al., "Autophagy as a Regulated Pathway of Cellular Degradation," Science, Dec. 1, 2000, 290:1717-1721.

Krishan et al., "Rapid flow cytofluorometric analysis of mammalian cell cycle by propidium iodide staining," J. Cell Biology, 1975, 66:188-193.

Lev et al., "Exposure of Melanoma Cells to Dacarbazine Results in Enhanced Tumor Growth and Metastasis In Vivo," J. Clin. Oncology, Jun. 1, 2004, 22(11):2092-2100.

Levade et al., "Ceramide in Apoptosis: A Revisited Role," Neurochemical Research, Aug. 2002, 27(7/8):601-607.

Li et al., "Chemotherapy-induced apoptosis in melanoma cells is p53 dependent," Melanoma Research, 1998, 8:17-23.

Martin, O., "Iminosugars: current and future therapeutic applications," Annales Pharmaceutiques Francaises, Jan. 2007, 65(1):5-13, with English abstract.

Mizushima, Noboru, "Methods for monitoring autophagy," Intl. J. Biochem. & Cell Biology, 2004, 36:2491-2502.

Morton et al., "Vaccine Therapy for Malignant Melanoma," CA Cancer J. Clin., 1996, 46:225-244.

Negroiu et al., "Folding and Maturation of Tyrosinase-related Protein-1 Are Regulated by the Post-translational Formation of Disulfide Bonds and by N-Glycan Processing," J. Biol. Chem., Oct. 13, 2000, 275(40):32200-32207.

Negroiu et al., "Protein specific N-glycosylation of tyrosinase and tyrosinase-related protein-1 in B16 mouse melanoma cells," Biochem. J., 1999, 344:659-665.

Negroiu et al., "The Inhibition of Early N-Glycan Processing Targets TRP-2 to Degradation in B16 Melanoma Cells," J. Biol. Chem., Jul. 18, 2003, 278(29):27035-27042.

O'Reilly et al., "Temozolomide: A New Oral Cytotoxic Chemotherapeutic Agent with Promising Activity Against Primary Brain Tumours," Eur. J. Cancer, 1993, 29A(7):940-942.

Paglin et al., "A Novel Response of Cancer Cells to Radiation Involves Autophagy and Formation of Acidic Vesicles," Cancer Research, Jan. 15, 2001, 61:439-444.

Petrescu et al., "Tyrosinase and Glycoprotein Folding: Roles of Chaperones That Recognize Glycans," May 9, 2000, 39(18):5229-5237.

Richards et al., "Effective Chemotherapy for Melanoma After Treatment with Interleukin-2," Cancer, Jan. 15, 1992, 69(2):427-429.

Rubtsova et al., "Disruption of active microfilaments by cytochalasin D leads to activation of p53," FEBS Letters, 1998, 430:353-357.

Rucklidge et al., "Cell-adhesion molecules and metalloproteinases: a linked role in tumour cell invasiveness," Biochemical Society Transactions, 648th Meeting, Belfast, Feb. 1994, 22(1), 7 pages.

Sawada et al., "Betulinic acid augments the inhibitory effects of vincristine on growth and lung metastasis of B16F10 melanoma cells in mice," British Journal of Cancer, 2004, 90:1672-1678.

Scarlatti et al., "Ceramide-mediated Macroautophagy Involves Inhibition of Protein Kinase B and Up-regulation of Beclin 1," J. Biol. Chem., Apr. 30, 2004, 279(18):18384-18391.

Stover et al., "Systemic Delivery of Liposomal Short-Chain Ceramide Limits Solid Tumor Growth in Murine Models of Breast Adenocarcnoma," Clin. Cancer Res., May 1, 2005, 11(9):3465-3474.

Stütz et al., "Iminosugars as Glycosidase Inhibitors, Nojirymycin and Beyond," 1999, Table of Contents, 8 pages.

Van Engeland et al., "Annexin V-Affinity Assay: A Review on an Apoptosis Detection System Based on Phosphatidylserine Exposure," Cytometry, 1998, 31:1-9.

Yamazaki et al., "Regulation of cancer cell motility through actin reorganization," Cancer Soc., Jul. 2005, 96(7):379-386.

Yao et al., "Molecular response of human glioblastoma multiforme cells to ionizing radiation: cell cycle arrest, modulation of the expression of cyclin-dependent kinase inhibitors, and autophagy," J. Neurosurg., 2003, 98:378-384.

Zhang et al., "Disruption of G1-phase phospholipid turnover by inhibition of $Ca^{2+}$-independent phospholipase $A_2$ induces a p53-dependent cell-cycle arrest in G1 phase," J. Cell Science, 2006, 119(6):1005-1015.

Ziegler-Heitbrock et al., "In Vitro Differentiation of Human Melanoma Cells Analyzed with Monoclonal Antibodies," Cancer Research, Mar. 1985, 45:1344-1350.

Goss et al., "A Phase I Study of Swainsonine in Patients with Advanced Malignancies," Cancer Research, Mar. 15, 1994, 54:1450-1457.

NCI Factsheet, "Targeted Cancer Therapies: Questions and Answers," published online Dec. 2005, 1-3.

* cited by examiner a: $R^1 = CH_3$; b: $R^1 = C_4H_9$;
c: $R^1 = C_8H_{17}$

12

11

10

COMBINATORIAL LIBRARY APPROACH TO IMINOCYCLITOLS WITH BIOLOGICAL ACTIVITY

CROSS-REFERENCE

The present application is a Divisional of U.S. application Ser. No. 11/514,339, filed Sep. 1, 2006, which claims priority to U.S. provisional application No. 60/713,344 filed Sep. 2, 2005, each of which is incorporated herein by reference in its entirety.

BACKGROUND

Iminocyclitols are monosaccharides with the intraring oxygen replaced by an imino group and are of considerable interest in modern glycobiology, see e.g. Legler, G. *Adv. Carbohydr. Chem. Biochem.* 1990, 48, 319; Winchester, B.; Fleet, G. W. J. *Glycobiology* 1992, 2, 199; Look, G. C.; Fotsch, C. H.; Wong, C. H. *Acc. Chem. Res* 1993, 26, 182; Ganem, B. *Acc. Chem. Res* 1996, 29, 340; Stutz, A. E. *Angew. Chem.* 1996, 108, 2054; *Angew. Chem. Int. Ed. Engl.* 1996, 35, 1926; O'Hagan, D. *Nat. Prod. Rep.* 1997, 14, 637; Bols, M. *Acc. Chem. Res.* 1998, 31, 1; Heightman, T. D.; Vasella, A. T. *Angew. Chem. Int. Ed. Engl.* 1999, 38, 750; Stütz, A. E. *Iminosugars as Glycosidase Inhibitors: Nojirimycin and Beyond*; Ed. Wiley-VCH: Weinheim, 1999, 157; Asano, N.; Nash, R. J.; Molyneux, R. J.; Fleet, G. W. J. *Tetrahedron: Asymmetry* 2000, 11, 1645; Pearson, M. S. M.; Mathé-Allainmat, M.; Fargeas, V.; Lebreton, J. *Eur. J. Org. Chem.* 2005, 2159; all incorporated herein by reference in their entirety. Recently, five-membered iminocyclitols have assumed high biological significance, even eclipsing that of the better known deoxynojirimycin (DNJ) and deoxygalactojirimycin (DGJ) as selective inhibitors of glycosidase and glucotransferases, see e.g. Mehta, A.; Ouzounov, S.; Jordan, R.; Simsek, E.; Lu, X.; Moriarty, R. M.; Jacob, G.; Dwek, R. A.; Block, T. M. *Antivir. Chem. Chemother.* 2002, 13(5), 299; Block, T. M.; Lu, X.; Platt, F. M.; Foster, G. R.; Gerlich, W. H.; Blumberg, B. S.; Dwek, R. A. *Proc. Natl. Acad. Sci. U.S.A.* 1994, 91(6), 2235; Branza-Nichita, N.; Durantel, D.; Carrouée-Durantel, S.; Dwek, R. A.; Zitzmann, N. *J. Virol.* 2001, 75(8), 3527; Durantel, D.; Branza-Nichita, N.; Carrouée-Durantel, S.; Butters, T. D.; Dwek, R. A.; Zitzmann, N. *J. Virol.* 2001, 75(19), 8987; Mehta, A.; Conyers, B.; Tyrrell, D. L. J.; Walters, K.-A.; Tipples, G. A.; Dwek, R. A.; Block, T. M. *Antimicrob. Agents and Chemother.* 2002, 46(12), 4004; Lu, X.; Tran, T.; Simsek, E.; Block, T. M. *J. Virol.* 2003, 77(22), 11933; Cook, C. S.; Karabatsos, P. J.; Schoenhard, G. L.; Karim, A. *Pharmaceutical Research* 1995, 12(8), 1158; all incorporated herein by reference in their entirety. Iminocyclitols are disclosed, for example, in U.S. Pat. No. 5,229,523 issued Jul. 20, 1993 to Wong et. al., in U.S. Pat. No. 5,276,120 issued Jan. 4, 1994, to Wong et. al., in U.S. Pat. No. 5,461,143 issued Oct. 24, 1995, to Wong et. al., in U.S. Pat. No. 5,596,005 issued Jan. 21, 1997, to Wong et. al., in U.S. Pat. No. 5,579,823 issued Jun. 2, 1998 to Wong et. al., in U.S. Pat. No. 6,232,450 issued May 15, 2001, to Wong, in U.S. Pat. No. 6,462,193 issued to Wong et. al. and in U.S. Pat. No. 6,774,140 issued Aug. 10, 2004, to Wong et. al. A biological activity of particular iminocyclitol compound can depend among other things on its stereochemical configuration and on substituent groups on the iminocyclitol ring. Combinatorial chemistry plays an important role in modern drug development as it allows to synthesize many different substances quickly for screening for a desired activity. It is highly desirable to apply combinatorial approach to the development of iminocyclitols with a particular biological activity. A combinatorial library of iminocyclitols was reported, for example, by Saotome et. al. in Chemistry & Biology v. 8, pp. 1061-1070, 2001, and in related US patent application publication No. 2004/0147591 to Kanie and Saotome. The iminocyclitols in these publications were synthesized using a Strecker method, which is a complicated method of synthesis. A combinatorial library of iminocyclitols was also disclosed by Chapman et. al. in Journal of American Chemical Society, v. 127, pp. 506-507, 2005, however, this combinatorial library did not provide alkyl substituents on the iminogroup, which is an obligatory element for antiviral activity. Thus, it is still highly desirable to develop a facile method of synthesizing of stereochemically defined iminocyclitols that allows for a variation of a large range of substituent groups.

SUMMARY

One embodiment of the invention is a method of synthesizing stereochemically defined iminocyclitol comprising replacing an intraring oxygen in a cyclic sugar by an intraring imine to form an iminocyclitol, wherein said iminocyclitol has a defined stereochemical configuration different from a stereochemical configuration of the cyclic sugar.

Another embodiment of the present invention is a stereochemically defined iminocyclitol compound or a salt thereof, wherein said compound having a formula selected from the group consisting of

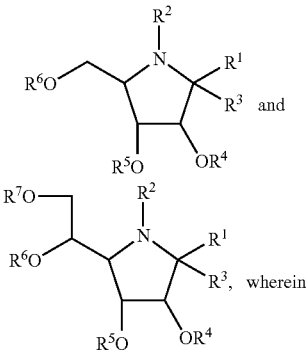

$R^1$ is an alkyl group comprising from 1 to 20 carbon atoms, $R^2$ is hydrogen or an alkyl group comprising from 1 to 20 carbon atoms, $R^3$ is hydrogen or an alkyl group comprising from 1 to 20 carbon atoms, $R^4$ is hydrogen or a first protecting group, $R^5$ is hydrogen or a second protecting group, $R^6$ is hydrogen or a third protecting group selected from the group consisting of methanesulfonate, tosylate and triflate; $R^7$ is hydrogen or a fourth protective group selected from the group consisting of t-butyldimethylsiloxy and tretyl radicals, wherein the first and the second protective form together isopropylidene or cyclohexylidene or are identical protective groups selected from the group consisting of benzyl, t-butyldimethylsiloxy radical and triphenylmethyl.

Yet another embodiment is a method of treating viral infection comprising contacting a cell infected with a virus causing the infection with one or more described above iminocyclitol compounds.

DETAILED DESCRIPTION

Figure 1:
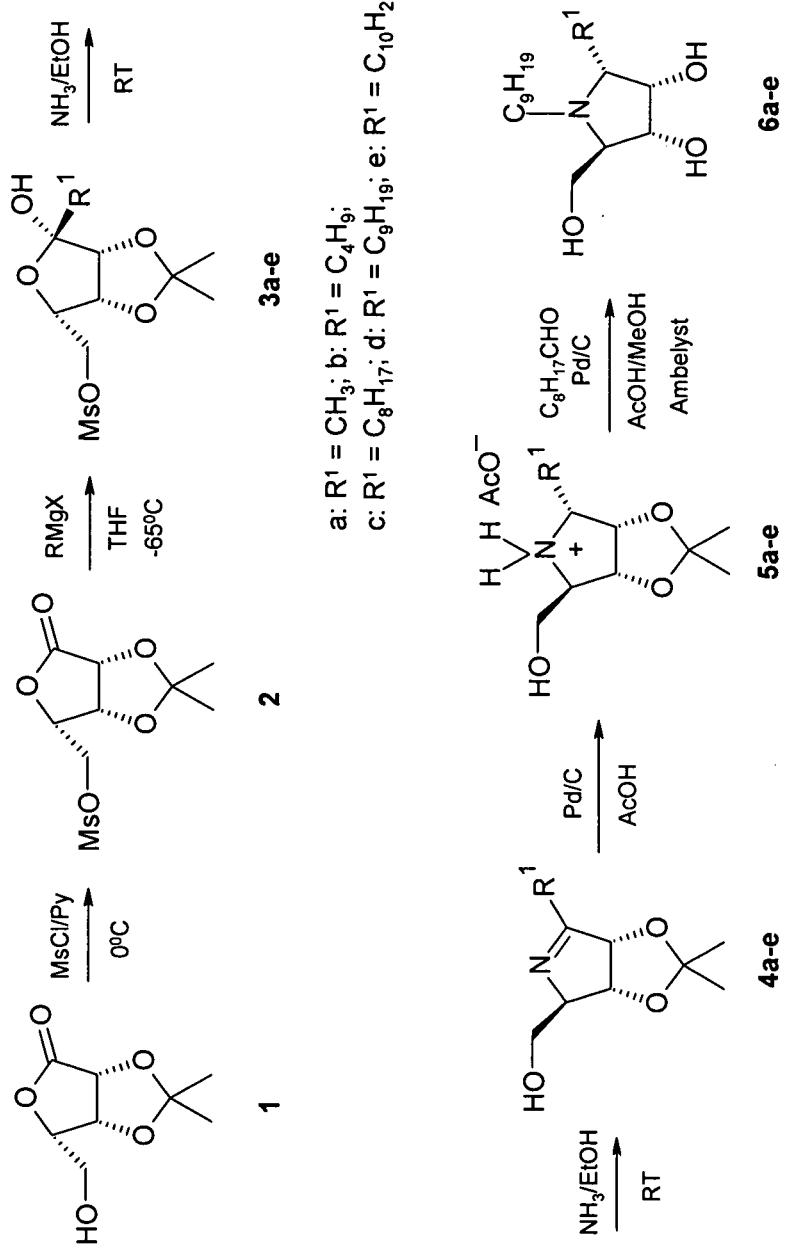
FIG. 1 illustrates a synthesis of N-alkyl-C-alkyl iminocyclitol in D-ribitol configuration from the starting lactone in L-lyxono configuration.

The present invention is directed to iminocyclitols with biological activity, a method of synthesizing the iminocyclitols, and, in particular, to a method of synthesizing stereochemically defined iminocyclitols from lactones.

Iminocyclitols are monosaccharides with the ring oxygen replaced by an imino group. Iminocyclitols can act as selective inhibitors and, therefore, can be used for treating metabolic disorders such as diabetes or as antiviral, antibacterial and anticancer agents. A biological activity of a particular iminocyclitol can depend among other things on its stereochemical configuration and on substituent groups on its ring. Method.

One embodiment of the present invention is a method of synthesizing stereochemically defined iminocyclitol comprising replacing an intraring oxygen of a cyclic sugar by an intraring imine to form the iminocyclitol, wherein said iminocyclitol, wherein the iminocyclitol has a stereochemical configuration different from a stereochemical configuration of the cyclic sugar. The replacement of the intraring oxygen by the intraring imine comprises reacting the cyclic sugar with a reagent comprising $NH_3$. The reagent for this reaction can further comprise, for example, methanol, ethanol, water, isopropyl alcohol, dioxan or a mixture thereof. The replacement of the intraring oxygen by the intraring imine can be performed at temperatures ranging from 110° C. to 30° C. but most preferably at room temperature. The cyclic sugar can be, for example, an aldopentose in a 4-deoxy 1,4 furanose form, an aldohexose in a 4-deoxy 1,4 furanose form or an aldohexose in a 2,5-dideoxy pyranose form. Preferably, the cyclic is substituted at the C1 carbon position by $R^1$ group. $R^1$ can be, for example, an alkyl group comprising from 1 to 20 carbon atoms. Preferably, all the hydroxyl groups of the cyclic sugar are protected by protective groups with the exception of the hydroxyl group on the C1 carbon. The cyclic sugar can be formed by reacting a protected lactone compound with a Grignard reagent $R^1MgX$, wherein X is a halide. The term "protected lactone" when used in the present application refers to a lactone having all hydroxyl groups protected by protective groups. The reaction between the protected lactone and $R^1MgX$ can be performed, for example, in tetrahydrofurane (THF) at the temperature ranging from −75° C. to 5° C., but most preferably, from −70° C. to −60° C. The protected lactone can be formed from an unprotected lactone. The iminocyclitol formed by replacing the intraring oxygen by the intraring imine can be further transformed into a hydrogenated iminocyclitol by hydrogenating the iminocyclitol. The hydrogenation of iminocyclitol can be carried out in the presence of a catalyst. The catalyst for the hydrogenation can comprise, for example, Pd, C, acetic acid (AcOH) or a combination thereof. The hydrogenated iminocyclitol can be then turned into a N-alkyl-C-alkyl iminocyclitol. The resulting N-alkyl-C-alkyl iminocyclitol has a substituent group $R^2CH_2$ on its nitrogen atom. The formation of the N-alkyl-C-alkyl iminocyclitol can be carried out, for example, by reacting the hydrogenated iminocyclitol with an aldehyde $R^2CHO$. This reaction can be carried in the presence of a catalyst which can comprise Pd, C, AcOH, MeOH, amberlyst catalyst or a combination thereof. The amberlyst catalyst can be, for example, Amberlyst A-21 ion exchange resin. The $R^2$ group of the aldehyde can be, for example, a hydrogen or an alkyl group comprising 1 to 20 carbon atoms. In some embodiments, the N-alkyl-C-alkyl iminocyclitol can have some of the hydroxyl groups still being protected by protective groups. In this case, the method of the present invention can further comprise deprotecting of the protected hydroxyl groups. Deprotecting of the protected hydroxyl groups can be carried out using, for example, trifluoroacetic acid $CF_3COOH$ on a water solution.

Figure 14:
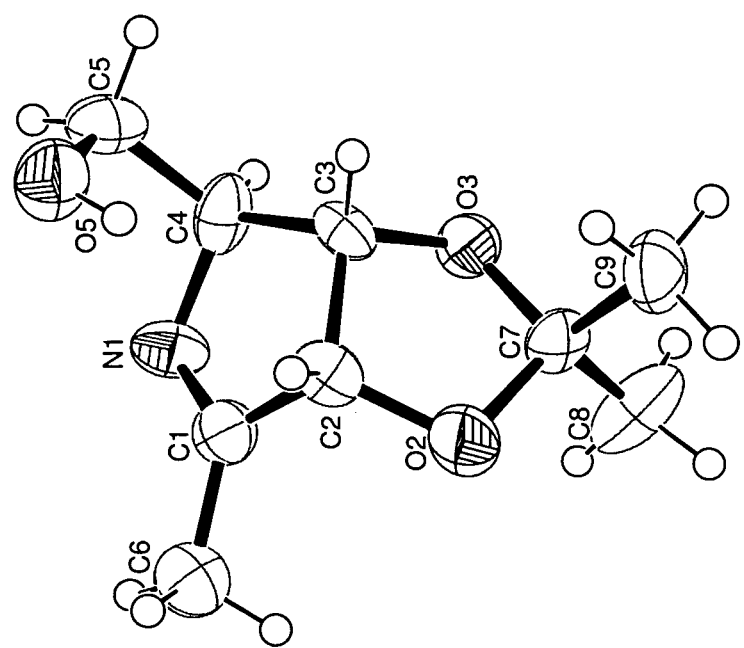
FIG. 14 shows the X-ray structure of the compound 4.

FIG. 1 illustrates a synthesis of a N-alkyl-C-alkyl iminocyclitol (compound 6) in D-ribitol stereochemical configuration from L-lyxonolactone in a 4-deoxy 1,4 furanose form. Reaction 1→2 is the protection of the hydroxyl group on by methane sulfonate radical to form the protected L-lyxonolactone-2,3-O-iospropylidene-6-methanesulfonate (compound 2). Reaction 3→4 comprises the replacement of the intraring oxygen by the intraring imine. This reaction leads to the rearrangement of the stereochemical configuration. The X-ray structure of the iminocyclitol (compound 4) is shown on the FIG. 14. The catalytic hydrogenation (reaction 4→5) yields compound 5 in D-ribitol stereochemical configuration. Reductive amination is illustrated as reaction 5→6.

Figure 3:
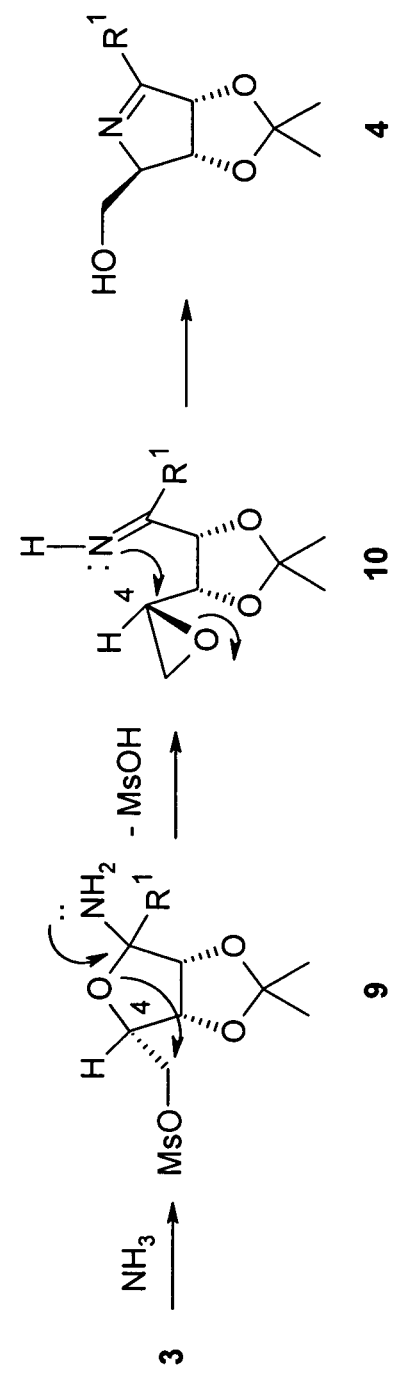
FIG. 3 illustrates a mechanism of the rearrangement of the C4 substituent and a $R^1$ group on the C1 carbon during the replacement of the intraring oxygen with an imino group.

The mechanism of the inversion of the stereochemical configuration is illustrated on FIG. 3. The intermediate epoxide 10 is formed as shown (9→10) and has retained configuration at C4. Subsequent intramolecular ring opening of the epoxide by the iminogroup is a favorable 5-exo-tet process resulting in inversion of configuration at C4.

Figure 2:
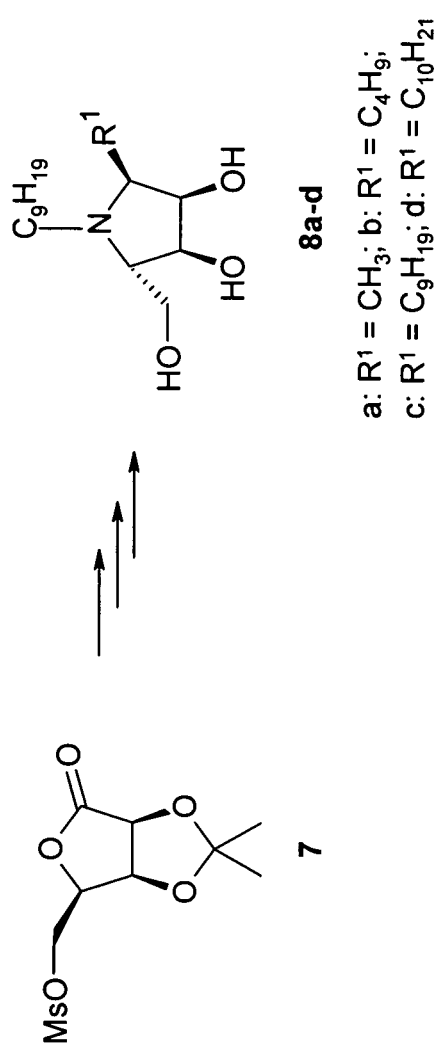
FIG. 2 illustrates a synthesis of N-alkyl-C-alkyl iminocyclitol in a L-ribitol configuration from the starting lactone in D-lyxono configuration.

FIG. 2 shows another embodiment of the invention. In particular, FIG. 2 illustrates the synthesis of N-alkyl-C-alkyl iminocyclitol (compound 8) in L-ribitol stereochemical configuration from D-lyxonolactone-2,3-O-propylidene-6-methanesulfonate (compound 7).

Figure 4:
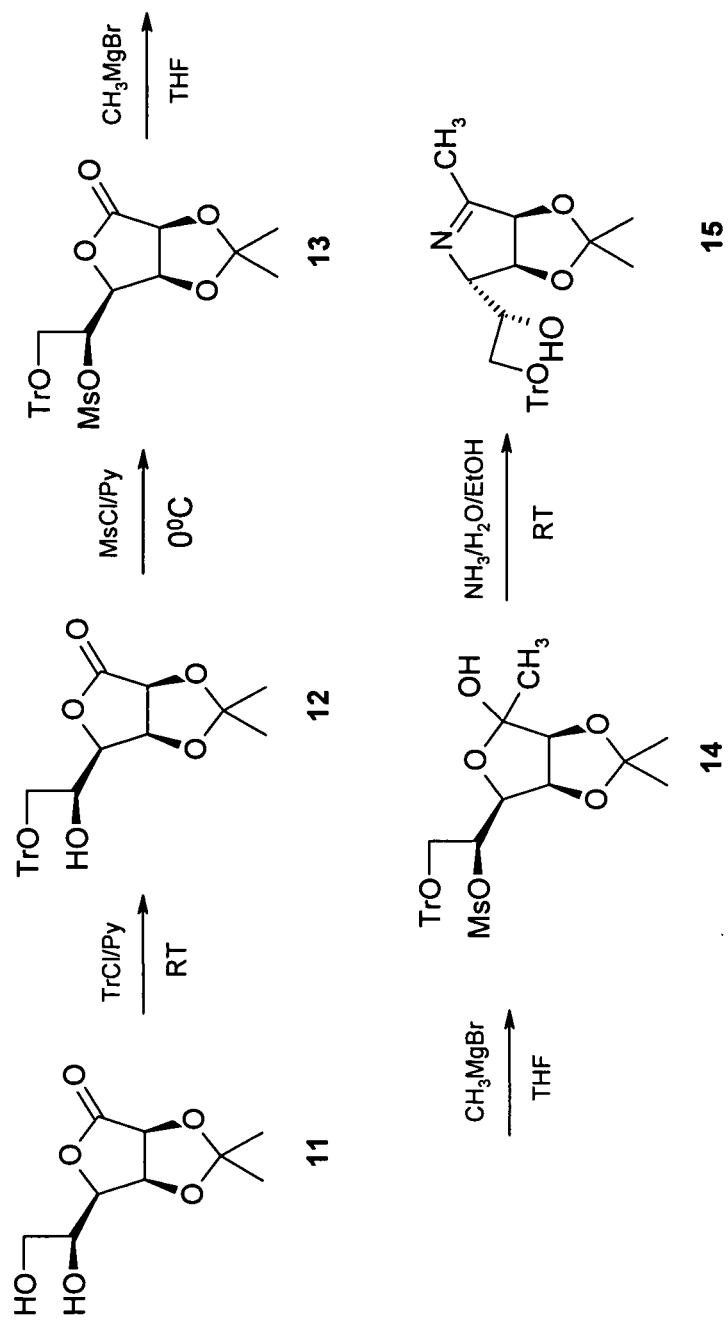
FIG. 4 illustrates a synthesis of iminocyclitol in a L-allonitol configuration from a starting lactone in a D-mannono configuration.
Figure 5:
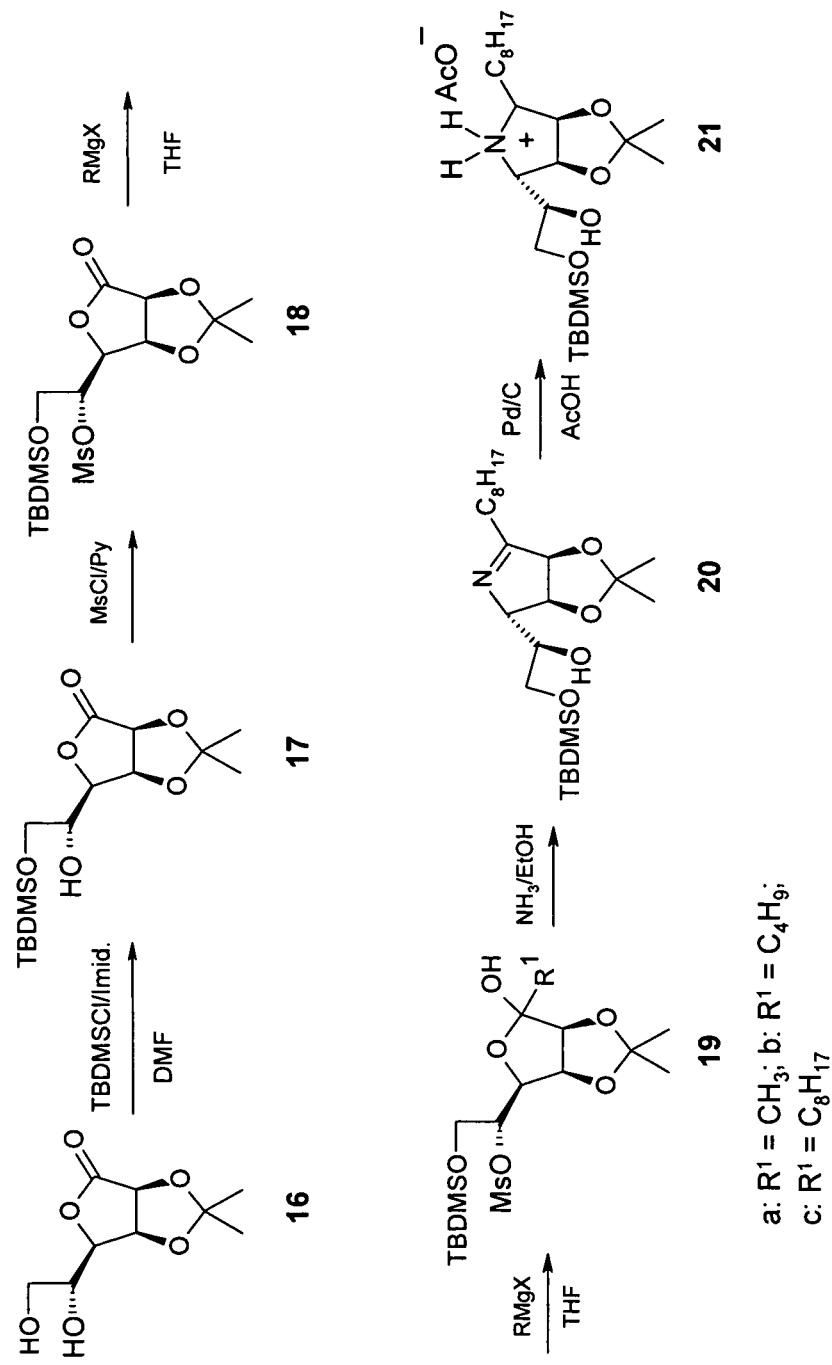
FIG. 5 illustrates a synthesis of iminocyclitol in D-talonitol configuration from a starting D-mannonolactone.

FIGS. 4 and 5 illustrate the present invention as directed to syntheses of iminocyclitols from hexose lactones in a 4-deoxy 1,4 furanose form. In particular, FIG. 4 shows a synthesis starting with a lactone in D-mannono stereochemical configuration to form an iminocyclitol in L-allonitol stereochemical configuration. 2,3-O-isopropylidene-D-mannonol 1,4 lactone is reacted (compound 11) with trityl chloride (TrCl) in pyridine (Py) to protect C6 primary hydroxyl group (reaction 11→12). The protected lactone (compound 13) of this embodiment is formed by mesylation, i.e. by reacting with methanesulfonate chloride (reaction 12→13). The protected lactone is then reacted (13→14) with a Grignard reagent $R^1MgX$ to form a cyclic sugar (compound 14). Replacing the intraring oxygen by an intraring imine (14→15) is accompanied by the change of the stereochemical configuration. In a particular case of hexose in a 4-deoxy 1,4 furanose form, this change includes a double inversion since both C5 and C5 hydroxyl group change a configuration with respect to C2 and C3 hydroxyl groups. Steps 15→16 and 16→17 respectively illustrate hydrogenation of the iminocyclitol and transformation of the hydrogenated iminocyclitol into N-alkyl-C-alkyl iminocyclitol accompanied by deprotecting of protective hydroxyl-groups.

FIG. 5 shows a synthesis of an iminocyclitol in D-talonitol stereochemical configuration starting with a lactone in a L-gulono stereochemical configuration. C6 primary hydroxyl group of 2,3-O-isopropylidene-L-gulono-1,4-lactone (compound 18) is protected by reacting with t-butyldimethylsiloxy chloride (TBDMSCl) (reaction 18→19) in imidazole and N,N-dimethylformamide (DMF). The protected lactone (compound 19) of this embodiment is further formed by mesylation (19→20). The reaction between the protected lactone and a Grignard reagent $R^1MgX$ (20→21) results in a formation of a cyclic sugar (compound 21). The replacement of the intraring oxygen of the cyclic sugar by an intraring imino group is illustrated by reaction 21→22. This replacement is accompanied by a double inversion of a stereochemical configuration, i.e. by change of the configuration of both C5 carbon and C5 hydroxyl group with respect to the C2 and C3 hydroxyl group.

Figure 12:
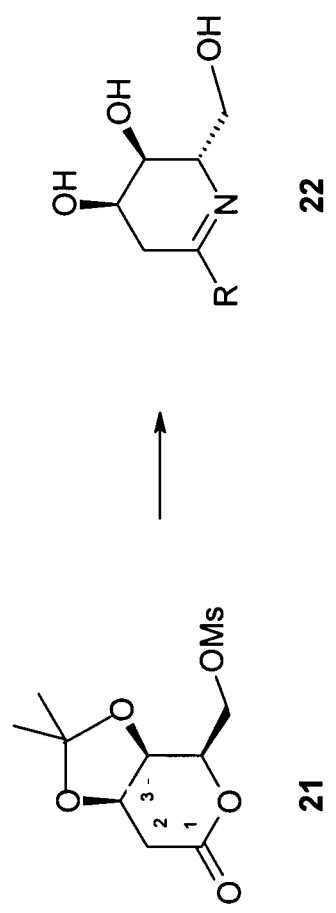
FIG. 12 illustrates the replacement of the intraring oxygen by imino group in a six-membered ring lactone

The invention as directed to a synthesis of iminocyclitol from a lactone to a 2,5-dideoxy 1,5 pyranose form is illustrated on FIG. 12. In this particular embodiment, a protected lactone (compound 38) has D-galono stereochemical configuration and the iminocyclitol (compound 39) has L-allonitol stereochemical configuration.

Figure 8:
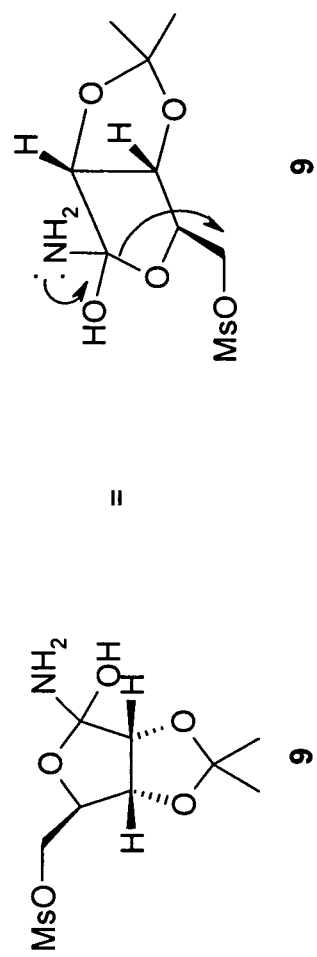
FIG. 8 illustrates Thorpe-Ingold effect.
Figure 9:
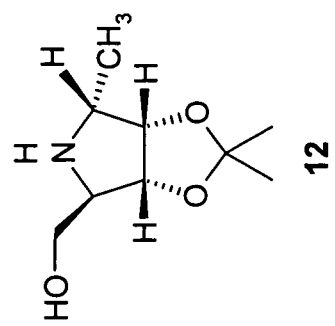
FIG. 9 illustrates how isopropylidene group controls the direction of catalytic hydrogenation.
Figure 9:
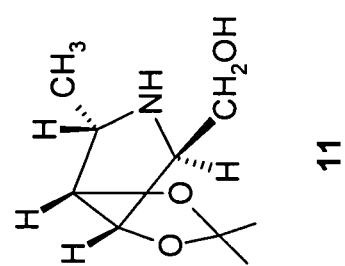
Figure 9:
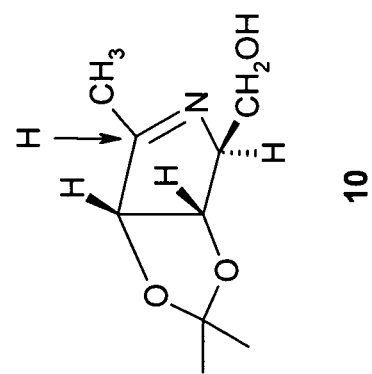

In some embodiments of the present invention, C2 and C3 hydroxyl groups can be protected by isopropylidene. FIGS. 8 and 9 illustrate advantages of using 2,3-isopropylidene as a protective group in a synthesis of iminocyclitols in a 2,3-cis-dihydroxypyrrolidine form. FIG. 8 shows how 2,3-iospropylidene forces the molecule into rigid cis-bicyclo[3.3.0]octyl ring system (compound 9) which may be optimal for the intermolecular cyclization (Thoape-Ingold effect). FIG. 9 demonstrates that the isoprolidene group can control the direction of catalytic hydrogenation since hydrogen must be added from the face opposite of the isopropylidene group.

Figure 10:
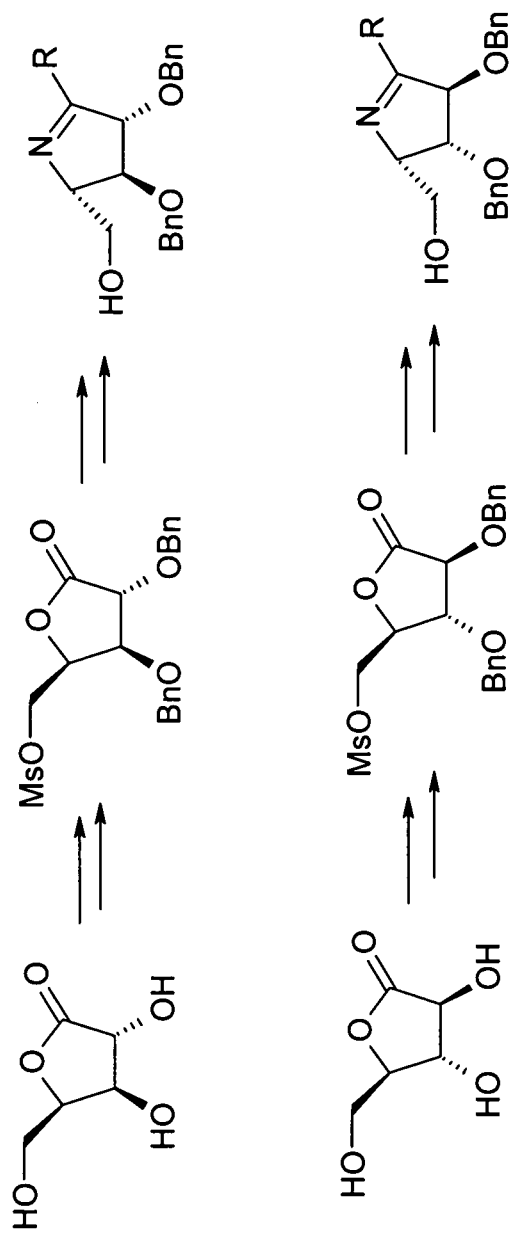
FIG. 10 illustrates a synthesis of iminocyclitols having hydroxyl groups on C2 and C3 carbons in trans conformation.
Figure 11:
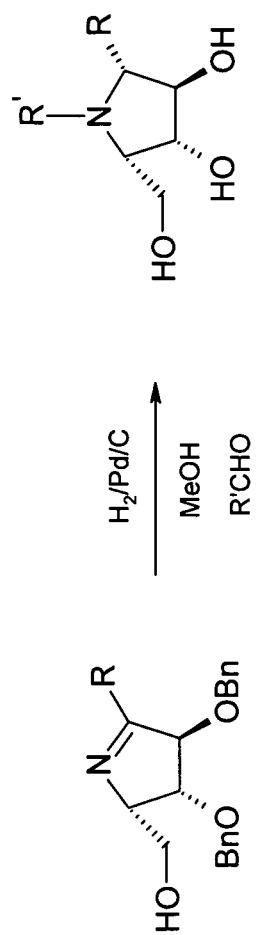
FIG. 11 illustrates catalytic hydrogenation, reductive amination for iminocyclitol having the hydroxyl groups on C2 and C3 carbons in trans conformation.

The method of the present invention directed to a synthesis of stereochemically defined 2,3-trans-dihydropyrrolidines is illustrated on FIG. 10. In particular, FIG. 10(a) illustrates a synthesis of an iminocyclitol in L-arabinitol stereochemical configuration (compound 30) from a lactone in D-xylono stereochemical configuration (compound 32), while FIG. 10(b) illustrates a synthesis of an iminocyclitol in L-xylitol stereochemical configuration from a lactone in D-arabinono stereochemical configuration. Protected lactones of these two embodiments are compounds 31 and 34, respectively. In these protected lactones, C2 and C3 hydroxyl groups are protected by benzyl radicals and C5 hydroxyl group is protected by a mesyl group. The iminocyclitol compounds 32 and 35 have stereochemical configurations inverted from stereochemical configurations of the respective protected lactones. FIG. 11 illustrates hydrogenating the iminocyclitol in L-xylitol stereochemical configuration, reacting the hydrogenated iminocyclitol with an aldehyde and deprotecting C2 and C3 hydroxyl groups of the N-alkyl-C-alkyl iminocyclitol (compound 37) carried out simultaneously.

Figure 13:
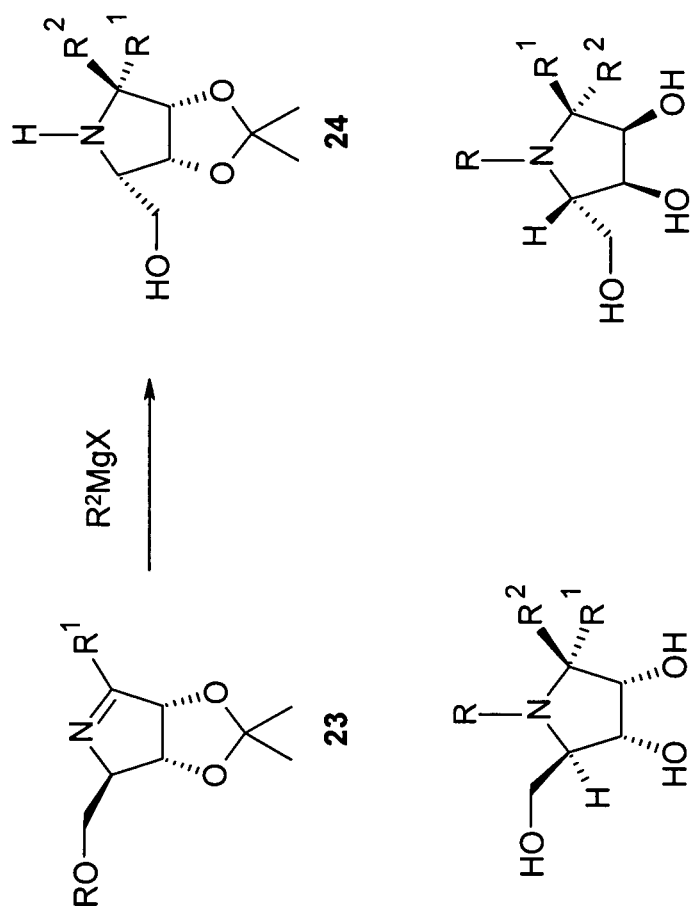
FIG. 13 illustrates a nucleophilic addition of $R^3$ group on C1 carbon.

In some embodiments, the method of the present invention can further comprise a nucleophilic addition of a second alkyl group $R^3$ to the C1 carbon of the iminocyclitol formed by replacing an intraring oxygen of the cyclic sugar by an intraring imine. The addition of the second alkyl to the C1 carbon of the iminocyclitol can be preceded by protecting the unprotected hydroxyl group on the iminocyclitol to form a protected iminocyclitol. The addition of the second alkyl to the C1 of the iminocyclitol can comprise reacting the protected iminocyclitol with a second Grignard reagent $R^3MgX$, wherein $R^3$ is an alkyl group comprising 1 to 20 carbons. Reaction between the protected iminocyclitol in D-ribitol stereochemical configuration and a second Grignard reagent $R^3MgX$ is illustrated on FIG. 13 (40→41). FIG. 13 also shows iminocyclitol compounds 42 and 43 that can be formed by the addition of the second alkyl group to the C1 carbon.

Figure 6:
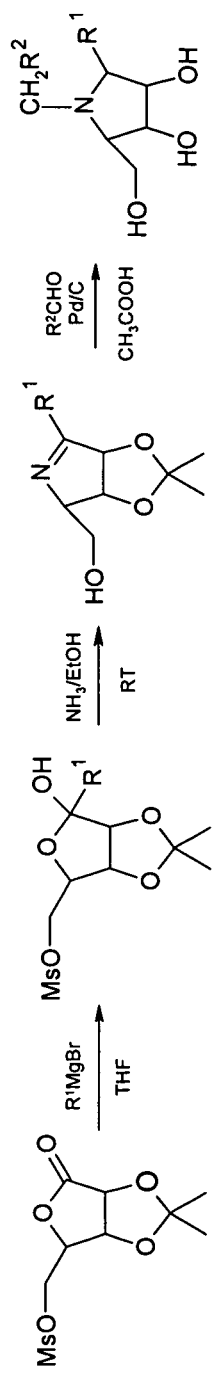
FIG. 6 illustrates how the reduction of the imino double bond, reductive alkylation and isopropylidene deprotection can be done in one step.
Figure 7:
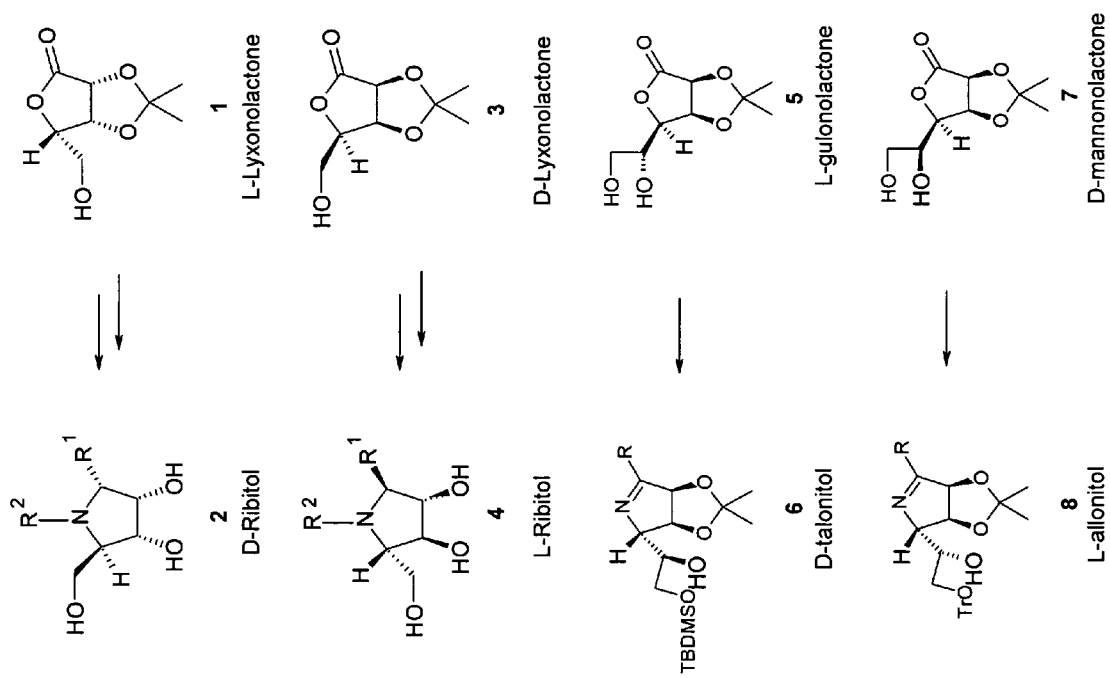
FIG. 7 illustrates possible combinations of stereochemical configurations of the starting lactone and resulting N-alkyl-C-alkyl-iminocyclitol.

One advantage of the present invention is that hydrogenating the iminocyclitol, reacting the hydrogenated iminocyclitol with an aldehyde and deprotecting C2 and C3 hydroxyl groups of the N-alkyl-C-alkyl iminocyclitol can be carried out simultaneously under catalytic hydrogenation conditions as illustrated on FIG. 6. This advantage can allow for applying the method of the present invention for a synthesis of a combinatorial library of N-alkyl-C-alkyl iminocyclitol compounds. Possible libraries of N-alkyl-C-alkyl iminocyclitol compounds in 2,3-cis-dihydroxypyrrolidine state are illustrated on FIG. 7 together with their respective starting lactones.

The protecting groups of hydroxyl group used herein are not particularly limited, and persons skilled in the art can select adequate examples thereof. Specific examples of protecting groups of hydroxyl group are listed below, but are not limited thereto: (ether type) methyl, methoxymethyl, methylthiomethyl, benzyloxymethyl, t-butoxymethyl, 2-methoxyethoxymethyl, 2,2,2-trichloroethoxymethyl, bis(2 chloroethoxy)methyl, 2-(trimethylsilyl)ethoxymethyl, tetrahydropyranyl, 3-bromotetrahydropyranyl, tetrahydrothiopyranyl, 4-methoxytetrahydropyranyl, 4-methoxytetrahydrothiopyranyl, 4-methoxytetrahydrothiopyranyl S,S-dioxide, tetrahydrofuranyl, and tetrahydrothiofuranyl; 1-ethoxyethyl, 1-methyl-1-methoxyethyl, 1-(isopropoxy)ethyl, 2,2,2-trichloroethyl, 2-(phenylselenyl)ethyl, t-butyl, allyl, cinnamyl, p-chlorophenyl, benzyl, p-methoxybenzyl, o-nitrobenzyl, p-nitrobenzyl, p-halobenzyl, p-cyanobenzyl, 3-methyl-2-picolyl N-oxide, diphenylmethyl, 5-dibenzosuberyl, triphenylmethyl, alpha.-naphthyldiphenylmethyl, p-methoxyphenyldiphenylmethyl, p-(p'-bromophenacyloxy) phenyldiphenylmethyl-1,9-anthryl, 9-(9-phenyl)xanthenyl, 9-(9-phenyl-10-oxo)anthryl, benzisothiazolyl S,S-dioxide; and trimethylsilyl, triethylsilyl, isopropyldimethylsilyl, t-butyldimethylsilyl (TMDMS), (triphenylmethyl)dimethylsilyl, t-butyldiphenylsilyl, methyldiisopropylsilyl, methyl di-t-butylsilyl, tribenzylsilyl, tri-p-xylylsilyl, triisopropylsilyl, and triphenylsilyl; (ester type) formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 2,6-dichloro-4-methylphenoxyacetate, 2,6-dichloro-4-(1,1,3,3-tetramethylb-utyl)phenoxyacetate, 2,4-bis(1,1-dimethylpropyl)phenoxyacetate, chlorodiphenylacetate, p-P-phenylacetate, 3-phenylpropionate, 3-benzoylpropionate, isobutyrate, monosuccinoate, 4-oxopentanoate, pivaloate, adamantoate, crotonate, 4-methoxycrotonate, (E)-2-methyl-2-butenoate, benzoate, o-(dibromomethyl)benzoate, o-(methoxycarbonyl)benzoate, p-phenylbenzoate, 2,4,6-trimethylbenzoate, p-P-benzoate, and alpha.-naphthoate; (carbonate type) methyl carbonate, ethyl carbonate, 2,2,2-trichloroethyl carbonate, isobutyl carbonate, vinyl carbonate, allyl carbonate, cinnamyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, and S-benzyl thiocarbonate; an(others) N-phenylcarbamate, N-imidazolylcarbamate, borate, nitrate, N,N,N',N'-tetramethylphosphorodiamidate, and 2,4-dinitrophenyl-sulfenate.

Methods for introducing or deprotecting the aforementioned protecting groups are known to persons skilled in the art and are described in, for example, Teodora, W. Green, Protective Groups in Organic Synthesis, John Wiley & Sons, Inc. (1981).

The method of the present invention can be also used for synthesis of iminocyclitols with a substituent on the C1 carbon atom. The substituent can be, for example, aryl or heteroaryl. The $C_1$ aryl compounds are powerful inhibitors for the nonspecific nucleoside N-ribohydrolases, see e.g. a) Horenstein, B. A; Zabinski, R. F.; Schramm, V. L. *Tetrahedron Lett.* 1993, 34, 7213; b) Fumeaux, R. H.; Limberg, G.; Tyler, P. C.; Schramm, V. L. *Tetrahedron* 1997, 53, 2915, both incorporated herein by reference in their entirety. The C1 nucleosides are called immucillins and are important purine nucleoside phosphorylase (PNP) inhibitors, see e.g. a) Evans, G. B.; Furneaux, R. H.; Gainsford, G. J.; Schramm, V. L.; Tyler, P. C. *Tetrahedron* 2000, 56, 3053; b) Evans, G. B.; Furneaux, R. H.; Hutchison, T. L.; Kezar, H. S.; Morris, P. E. Jr.; Schramm, V. L.; Tyler, P. C. *J. Org. Chem.* 2001, 66, 5723; c) Ting, L.-M.; Shi, W.; Lewandowicz, A.; Singh, V.; Mwakingwe, A.; Birck, Ma. R.; Ringia, E. A. T.; Bench, G.; Madrid, D. C.; Tyler, P. C.; Evans, G. B.; Furneaux, R. H.; Schramm, V. L.; Kim, K. *J. Biol. Chem.* 2005, 280(10), 9547, all incorporated herein by reference in their entirety. C1 substituted iminocyclitols are usually synthesized from 5-O-TBDMS-1-N-dehydro-1,4-imino-2,3-O-isopropylidene-D-ribitol, which is formed by dehydrochlorination of the N-chloroamine, and subsequent nucleophilic addition of lithium alkyls, aryls and heteroaryls, see e.g. Chapman, T. M.; Davies, I. G.; Gu, B.; Block, T. M.; Scopes, D. I. C.; Hay. P. A.; Courtney, S. M.; McNeill, L. A.; Schofield, C. J.; Davis, B. G. *J. Am. Chem. Soc.* 2005, 127, 506, incorporated herein by reference in its entirety. In the method of the present invention, the C1 substituent is installed at an earlier stage and the troublesome dimerization and trimerization of C1 unsubstituted 1-N-pyrrolidines as starting materials is avoided, see e.g. Han, B.; Rajwanshi, V.; Nandy, J.; Krishnamurthy, R.; Eschenmoser, A. *Synlett* 2005, 5, 744, incorporated herein by reference in its entirety.

Iminocyclitol Libraries

The present invention also provides combinatorial libraries of stereochemically defined iminocyclitol compounds and the individual iminocyclitol compounds having a formula selected from the group consisting of

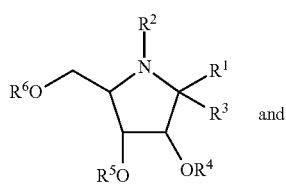

and

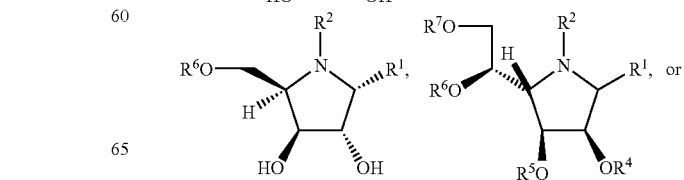

wherein $R^1$ is an alkyl group comprising from 1 to 20 carbon atoms or from 1 to 10 carbon atoms, $R^2$ is hydrogen or an alkyl group comprising from 1 to 20 carbon atoms or from 1 to 10 carbon atoms, $R^3$ is hydrogen or an alkyl group comprising from 1 to 20 carbon atoms or from 1 to 10 carbon atoms, $R^4$ is hydrogen or a first protecting group, $R^5$ is hydrogen or a second protecting group, $R^6$ is hydrogen or a third protecting group selected from the group consisting of methanesulfonate, tosylate and triflate.

$R^7$ is hydrogen or a fourth protective group selected from the group consisting of t-butyldimethylsiloxy and trityl radicals, wherein the first and the second protective form together isopropylidene, cyclohexylidene or are identical protective groups selected from the group consisting of benzyl, t-butyldimethylsiloxy radical and triphenylmethyl radical. In some embodiments, a stereochemical configuration of the iminocyclitol compound can be, but not limited to,

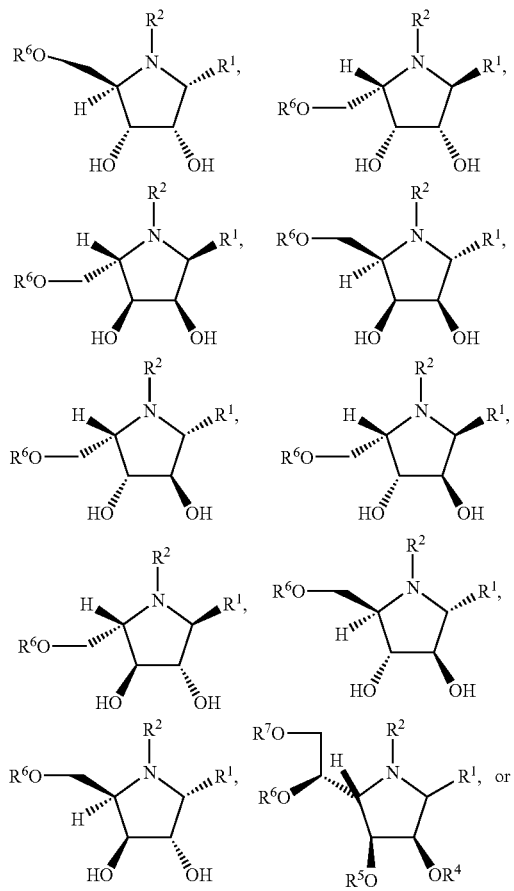

-continued

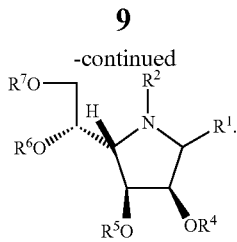

The present invention also provides an inhibitor sugar chain related enzymes comprising one or more of the above iminocyclitol compounds or a salt thereof. The present invention also provides a medicine or a pharmaceutical product comprising one or more of the above iminocyclitols or a salt thereof.

The medicine of the present invention is useful for treating or preventing diseases associated with sugar chain related enzymes. For example, it can be used as an antiviral agent, an anticancer agent, or an immunostimulant agent.

When the compound of the present invention is used as an inhibitor of sugar chain related enzymes, examples of target sugar chain related enzymes include glycolytic enzymes (such as glycohydrolase) and glycosyltransferase.

When the medicine of the present invention is used as an antiviral agent, the type of the target viral disease is not particularly limited. Diseases caused by virus infections include, for example, Japanese encephalitis, dengue fever, measles, epidemic parotitis, epidemic roseola, influenza, hepatitis A, hepatitis B, hepatitis C, yellow fever, hemorrhagic fever, meningitis, infantile diarrhea, rabies, Ebola hemorrhagic fever, Lassa fever, polio, St. Louis encephalitis, adult T cell leukemia, and AIDS. Examples of known intractable diseases that are deduced to be caused by virus infections include chronic rheumatism, systemic erythematodes, multiple sclerosis, subacute sclerosing panencephalitis, Alzheimer's disease, ulcerative colitis, Crohn's disease, Kawasaki disease, and diabetes. The antiviral agent of the present invention is useful for treating or preventing these diseases.

When the medicine of the present invention is used as an anticancer agent, a type of target tumor or cancer is not particularly limited. Examples thereof include all malignant and benign tumors, and includes carcinomas (epithelial malignant tumors), sarcomas (non-epithelial malignant tumors), and mixed types thereof.

The type of cancer can be classified based on the site that it developed in Specific examples of cancers include hypophyseal adenoma, neuroglioma, acoustic neuroma, brain tumor, pharyngeal cancer, laryngeal cancer, thymoma, mesothelioma, breast cancer, lung cancer, gastric cancer, esophageal cancer, colon cancer, hepatocellular cancer, pancreatic cancer, pancreatic endocrine tumor, cholangiocarcinoma, gallbladder cancer, penile cancer, ureteral cancer, renal cell carcinoma, orchioncus (testicular tumor), prostate cancer, bladder cancer, vulvar cancer, uterine cancer, uterine sarcoma, vaginal cancer, ovarian cancer, ovarian germ cell tumor, malignant melanoma, mycosis fungoides, skin cancer, soft part sarcoma, malignant lymphoma, non Hodgkin's lymphoma, myelodysplastic syndromes, multiple myeloma, plasma cell tumor, and brown lymphoma. The aforementioned examples represent examples of the cancers, and the cancers are not limited thereto.

The medicine of the present invention can be administered orally or parenterally (such as intravenous, intramuscular, hypodermic, or endodermic injection, intrarectal administration, or transmucosal administration). Examples of pharmaceutical compositions that are suitable for oral administration include tablets, granules, capsules, powders, solutions, suspensions, and syrups. Examples of pharmaceutical compositions that are suitable for parenteral administration include injections, drops, suppositories, and transdermal absorbents. The dosage forms of the medicine of the present invention are not limited thereto.

Types of the pharmaceutical additives that are used for producing the medicine of the present invention are not particularly limited, and persons skilled in the art can select adequate one. Examples of the pharmaceutical additives that can be used include excipients, disintegrators or disintegration assistants, binders, lubricants, coating agents, bases, solubilizers or solubilization assistants, dispersants, suspensions, emulsifiers, buffers, antioxidants, preservatives, isotonizing agents, pH regulators, solubilizers, and stabilizers. The specific ingredients of the pharmaceutical additives used for these purposes are well known to persons skilled in the art.

Examples of pharmaceutical additives that can be used for producing preparations for oral administration include: excipients such as glucose, lactose, D-mannitol, starch, or crystalline cellulose; disintegrators or disintegration assistants such as carboxymethyl cellulose, starch, or carboxy methylcellulose calcium; binders such as hydroxypropyl cellulose, hydroxypropyl methylcellulose, polyvinylpyrrolidone, or gelatin; lubricants such as magnesium stearate or talc; coating agents such as hydroxypropyl methylcellulose, sucrose, polyethylene glycol, or titanium oxide; and bases such as vaseline, liquid paraffin, polyethylene glycol, gelatin, kaolin, glycerin, purified water, or hard fat.

Examples of pharmaceutical additives that can be used for producing injection or drop preparations include: solubilizers or solubilization assistants that can constitute aqueous injections or injections to be dissolved before use, such as distilled water for injection, physiological saline, or propylene glycol; isotonizing agents such as glucose, sodium chloride, D-mannitol, or glycerin; and pH regulators such as inorganic acids, organic acids, inorganic bases, or organic bases.

The medicine of the present invention can be administered to mammal, including humans.

Applicability

The present invention provides novel iminocyclitol compounds. The iminocyclitol compounds of the present invention can be useful, for example, as a specific inhibitor of sugar chain related enzymes such as glycosyltransferase and glycosidase. The iminocyclitol compounds of the present invention can be useful, for example, as medicine for treating or preventing diseases associated with sugar chain related enzymes, and more specifically, they can be useful as antiviral agents, anticancer agents or as immunostimulant agents. Using combinatorial libraries of the present invention, novel enzyme inhibitors can be discovered. Iminocyclitol compounds of the present invention with defined stereochemical configuration can imitate different sugar through conformational changes, i.e. iminocyclitols of the present invention can select a more adequate conformation for an enzyme given by the induced fit. Therefore, compounds of the present invention provided as a combinatorial library can be useful for developing new pharmaceuticals.

The present invention also provides a method of treating a viral infection comprising contacting a cell infected with a virus causing the infection with one or more of the above disclosed iminocyclitols compounds. The virus can be for example a hepatitis virus, such as hepatitis C virus, hepatitis B virus or bovine viral diarrhea virus. The contacting of the cell can comprise administering the one or more iminocyclitols compounds to a subject such as mammal including human.

The following examples illustrate the present invention. However, it should be understood that the present invention is not limited thereto.

Example 1

Preparation of ((1R,2S,3R,4R)-1-$R^1$—N—$R^2$-2,3-diol-4-hydroxymethyl pyrrolidine)

In the Examples 1-4, melting points were determined using a Fisher Johns apparatus and are uncorrected. $^1$H nuclear magnetic resonance (NMR) spectra were determined with Bruker 400 spectrometer at 400 MHz. $^{13}$C NMR spectra were recorded with a Bruker 400 spectrometer at 75 MHz.

Step 1: Synthesis of 5-O-Methanesulfonyl-2,3-O-isopropylidene-L-lyxonolactone

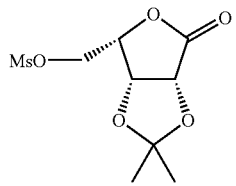 [SMILES: CC1(C)O[C@@H]2[C@H](COS(C)(=O)=O)OC(=O)[C@@H]2O1]

2,3-O-Isopropylidene-L-lyxono-1,4-lactone (a gift from United Therapeutic Corporation, 5 g, 26.6 mmol) was dissolved in pyridine (8 ml) and methanesulfonylchloride (2 ml, 29.2 mmol, 1.1 eq) was added to a stirred at 0° C. over 10 min. The mixture was kept at 0° C. for 1 h. 0.5 ml water was then added and the mixture was extracted with methylene chloride (15 ml). The extract was washed with HCl 10% (2×5 ml) and with aqueous NaHCO$_3$ (5 ml). The organic phase was dried (MgSO$_4$), filtered and evaporated under reduced pressure to yield 5-O-methanesulfonyl-2,3-O-isopropylidene-L-lyxonolactone (90%) as colorless crystals, m.p. 129-131° C. (lit mp 133-133.5° C., 79%).

$^1$H-nuclear magnetic resonance spectrum ($^1$H NMR) (400 MHz, CDCl$_3$) δ 4.89 (d, 2H, H-2, H-3), 4.79 (m, 1H, H-4), 4.56 (dd, $J_{5',5}$=11.7 Hz, $J_{5',4}$=4.1 Hz, 1H, H-5'), 4.48 (dd, $J_{5,5'}$=11.7 Hz, $J_{5,4}$=7.6 Hz, 1H, H-5), 3.11 (s, 3H, CH$_3$SO$_2$), 1.49 and 1.40 (2s, 6H, 2CH$_3$); $^{13}$C-NMR (75 MHz, CDCl$_3$) δ 172.9 (CO), 115.1 (C-6), 76.4 (C-2), 76.0 (C-4), 75.6 (C-3), 67.1 (C-5), 37.9 (CH$_3$SO$_2$), 26.9 and 25.9 (2CH$_3$).

For details of this procedure, see also Godskesen M.; Lundt I.; Madsen R.; Winchester B. *Bioorg. Med. Chem.* 1996, 4, 1857, incorporated herein by reference in its entirety.

Step 2: Synthesis of 1-$R^1$-5-O-methanesulfonyl-2,3-O-isopropylidene-L-lyxose

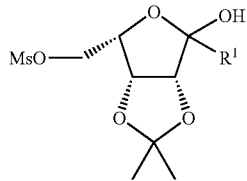

5-O-Methanesulfonyl-2,3-O-isopropylidene-L-lyxono-1,4-lactone (5 g, 18 mmol) was dissolved in tetrahydrofuran (THF) (125 ml) anhydrous under Ar. The solution was cooled to −68° C., maintaining the temperature between −50° C.~−40° C., the Grignard reagent (1.5 eq) was added with stirred over 20 min. The temperature was allowed to warm to 0° C. and the solution was stirred 1 h. After quenching with saturated aqueous NH$_4$Cl, the mixture was extracted with ethyl acetate (2×15 ml). The combined extracts were washed with saturated aqueous NH$_4$Cl, dried over Na$_2$SO$_4$, and filtered. Evaporation of the filtrate under vacuo afforded 1-$R^1$-5-O-methanesulfonyl-2,3-O-isopropylidene-L-lyxoses as a stereoisomer mixture at the anomeric carbon atom.

1-Methyl-5-O-methanesulfonyl-2,3-O-isopropylidene-L-lyxose, (93%) colorless crystals, m.p. 113-115° C. Ratio of isomers α:β~19:81. C$_{10}$H$_{18}$O$_7$S, M=282.31: MS m/z 305.1 (M+Na). $^1$H-NMR (400 MHz, CDCl$_3$) δβ: 4.83 (dd, $J_{3,2}$=5.8 Hz, $J_{3,4}$=3.7 Hz, 1H, H-3), 4.51 (dd, $J_{5',5}$=10.0 Hz, $J_{5',4}$=2.9 Hz, 1H, H-5'), 4.48 (d, $J_{2,3}$=5.8 Hz, 1H, H-2), 4.41-4.32 (m, 2H, H-4 and H-5'), 3.06 (s, 3H, CH$_3$SO$_2$), 1.54 (s, 3H, CH$_3$), 1.47 and 1.31 (2s, 6H, 2CH$_3$); α: 4.78 (dd, $J_{3,2}$=6.1 Hz, $J_{3,4}$=3.9 Hz, 1H, H-3), 4.52-4.45 (m, 1H, H-5'), 4.40-4.32 (m, 1H, H-2), 4.41-4.32 (m, 1H, H-5), 3.92 (m, 1H, H-4), 3.07 (s, 3H, CH$_3$SO$_2$), 1.54 and 1.36 (2s, 6H, 2CH$_3$), 1.41 (s, 3H, CH$_3$); $^{13}$C-NMR (75 MHz, CDCl$_3$) δβ: 112.9 (C-6), 107.3 (C-1), 85.2 (C-2), 80.4 (C-3), 76.7 (C-4), 68.1 (C-5), 37.5 (CH$_3$), 26.0 and 25.7 (2CH$_3$), 22.4 (CH$_3$).

1-Butyl-5-O-methanesulfonyl-2,3-O-isopropylidene-L-lyxose, (92%) colorless crystals, m.p. 54-55° C. Ratio of isomers α:β~23:77. C$_{13}$H$_{24}$O$_7$S, M=324.4. $^1$H-NMR (400 MHz, CDCl$_3$) δβ: 4.83 (dd, $J_{3,2}$=5.8 Hz, $J_{3,4}$=3.8 Hz, 1H, H-3), 4.53-4.32 (m, 4H, H-2, H-4, H-5', H-5), 3.06 (s, 3H, CH$_3$SO$_2$), 1.46 and 1.30 (2s, 6H, 2CH$_3$), 1.45-1.34 (m, 4H, CH$_2$), 1.88-1.68 (m, 2H, CH$_2$), 0.91 (m, 3H, CH$_3$); α: 4.77 (dd, $J_{3,2}$=5.9 Hz, $J_{3,4}$=4.1 Hz, 1H, H-3), 4.53-4.32 (m, 3H, H-2, H-5', H-5), 3.93 (m, 1H, H-4), 3.07 (s, 3H, CH$_3$SO$_2$), 1.54 and 1.36 (2s, 6H, 2CH$_3$); $^{13}$C-NMR (75 MHz, CDCl$_3$) δβ: 112.9 (C-6), 107.3 (C-1), 84.6 (C-2), 80.1 (C-3), 76.4 (C-4), 68.4 (C-5), 37.5 (CH$_3$SO$_2$), 34.9, 24.8, 22.9 (3CH$_2$), 26.0 and 25.4 (2CH$_3$), 14.0 (CH$_3$); α: 113.8 (C-6), 104.8 (C-1), 79.7 (C-3), 73.9 (C-4), 68.4 (C-5), 37.6 (CH$_3$SO$_2$), 25.8 and 24.6 (2CH$_3$), 13.8 (CH$_3$).

1-Octyl-5-O-methanesulfonyl-2,3-O-isopropylidene-L-lyxose, (90%) colorless oil. Ratio of isomers α:β~20:80. C$_{17}$H$_{32}$O$_7$S, M=380.5. $^1$H-NMR (400 MHz, CDCl$_3$) δβ: 4.82 (dd, $J_{3,2}$=5.9 Hz, $J_{3,4}$=3.6 Hz, 1H, H-3), 4.51 (dd, $J_{5',5}$=8.6 Hz, $J_{5',4}$=1.7 Hz, 1H, H-5'), 4.45 (d, $J_{2,3}$=5.9 Hz, 1H, H-2), 4.39-4.27 (m, 2H, H-4, H-5), 3.06 (s, 3H, CH$_3$SO$_2$), 1.45 and 1.30 (2s, 6H, 2CH$_3$), 1.45-1.24 (m, 12H, CH$_2$), 1.88-1.68 (m, 2H, CH$_2$), 0.88 (tl, 3H, CH$_3$); α: 4.77 (dd, $J_{3,2}$=6.0 Hz, $J_{3,4}$=3.9 Hz, H-3), 4.50-4.43 (m, H-5'), 4.39-4.27 (m, 2H, H-2, H-5), 3.93 (m, 1H, H-4), 3.07 (s, 3H, CH$_3$SO$_2$), 1.54 and 1.36 (2s, 6H, 2CH$_3$); $^{13}$C-NMR (75 MHz, CDCl$_3$) δβ: 113.0 (C-6), 107.4 (C-1), 84.7 (C-2), 80.3 (C-3), 76.5 (C-4), 68.7 (C-5), 37.6 (CH$_3$SO$_2$), 35.3, 32.0, 30.1, 29.6, 29.4, 23.4, 22.8 (7CH$_2$), 26.2 and 25.9 (2CH$_3$), 14.3 (CH$_3$); α: 113.8 (C-6), 104.8 (C-1), 79.8 (C-3), 74.0 (C-4), 68.4 (C-5), 37.6 (CH$_3$SO$_2$), 25.8 and 24.6 (2CH$_3$), 14.1 (CH$_3$).

1-Nonyl-5-O-methanesulfonyl-2,3-O-isopropylidene-L-lyxose, (94%) colorless oil. Ratio of isomers α:β~22:78. C$_{18}$H$_{34}$O$_7$S, M=394.53. $^1$H-NMR (400 MHz, CDCl$_3$) δβ: 4.82 (dd, $J_{3,2}$=5.8 Hz, $J_{3,4}$=3.4 Hz, 1H, H-3), 4.49 (dd, $J_{5',5}$=8.3 Hz, $J_{5',4}$=1.5 Hz, 1H, H-5'), 4.47 (d, $J_{2,3}$=5.8 Hz, 1H, H-2), 4.40-4.33 (m, 2H, H-4, H-5), 3.06 (s, 3H, CH$_3$SO$_2$), 1.88-1.68 (m, 2H, CH$_2$), 1.45 and 1.30 (2s, 6H, 2CH$_3$), 1.45-1.24 (m, 14H, CH$_2$), 0.88 (tl, 3H, CH$_3$); a: 4.78 (dd, $J_{3,2}$=6.0 Hz, $J_{3,4}$=3.9 Hz, H-3), 4.52-4.43 (m, H-5'), 4.40-4.33 (m, 2H, H-2, H-5), 3.93 (m, 1H, H-4), 3.07 (s, 3H, CH$_3$SO$_2$), 1.54 and 1.36 (2s, 6H, 2CH$_3$); $^{13}$C-NMR (75 MHz, CDCl$_3$) δβ: 112.8 (C-6), 107.2 (C-1), 84.5 (C-2), 80.1 (C-3), 76.3 (C-4), 68.4

(C-5), 37.4 (CH$_3$SO$_2$), 35.1, 31.8, 29.7, 29.5, 29.4, 29.3, 23.2, 22.6 (8CH$_2$), 25.9 and 25.8 (2CH$_3$), 14.1 (CH$_3$); α: 113.6 (C-6), 104.6 (C-1), 79.7 (C-3), 73.8 (C-4), 68.2 (C-5), 37.5 (CH$_3$SO$_2$), 25.8 and 24.6 (2CH$_3$), 14.1 (CH$_3$).

Step 3: Synthesis of ((2S,3R,4R)-1-R$^1$-2,3-isopropylidenedioxy-4-hydroxymethyl-1-pyrroline)

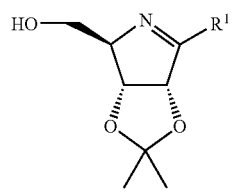

1-R-5-O-Methanesulfonyl-2,3-O-isopropylidene-L-lyxose (14 mmol) was dissolved in NH$_3$/EtOH 3:1 (50 ml). The solution was allowed to stand 2 days at room temperature in a sealed flask. The solvent was removed under reduced pressure, and the residue was dissolved in methanol (5 ml) and dried over Na$_2$SO$_4$, and filtered. Evaporation of the filtrate under vacuo afforded the crude product which was purified by silica gel column chromatography, eluting with ethyl acetate, to afford ((2S,3R,4R)-1-R$^1$-2,3-isopropylidenedioxy-4-hydroxymethyl-1-pyrrolines as colorless crystalline products.

((2S,3R,4R)-1-Methyl-2,3-isopropylidenedioxy-4-hydroxymethyl-1-pyrroline), colorless crystals, mp 104-5° C. (44%). C$_9$H$_{15}$NO$_3$, M=185.22: MS m/z 186.2 (M+H). $^1$H-NMR (400 MHz, CDCl$_3$) δ 4.9 (d, J$_{2,3}$=5.5 Hz, 1H, H-2), 4.6 (d, J$_{3,2}$=5.5 Hz, 1H, H-3), 4.16 (bs, 1H, H-4), 3.87 (dd, J$_{5',5}$=11.6 Hz, J$_{5',4}$=3.3 Hz, 1H, H-5'), 3.77 (dd, J$_{5',5}$=11.6 Hz, J$_{5,4}$=3.4 Hz, 1H, H-5), 2.09 (d, J$_{1,CH3}$=0.8 Hz, 3H, CH$_3$), 1.36 and 1.35 (2s, 6H, 2CH$_3$). $^{13}$C-NMR (75 MHz, CDCl$_3$) δ 176.0 (C=N), 111.7 (C-6), 87.2 (C-2), 80.7 (C-3), 77.9 (C-4), 62.2 (C-5), 25.7 (2CH$_3$), 16.9 (CH$_3$).

((2S,3R,4R)-1-Butyl-2,3-isopropylidenedioxy-4-hydroxymethyl-1-pyrroline), colorless crystals, mp 114-5° C. (54%). C$_{12}$H$_{21}$NO$_3$, M=227.3: MS m/z 228.3 (M+H); calcd for C$_{12}$H$_{21}$NO$_3$ (M+H)$^+$ 228.1600, found 228.1606. $^1$H-NMR (400 MHz, CDCl$_3$) δ 4.94 (d, J$_{2,3}$=5.5 Hz, 1H, H-2), 4.58 (d, J$_{3,2}$=5.5 Hz, 1H, H-3), 4.21 (bs, 1H, H-4), 3.88 (dd, J$_{5',5}$=11.4 Hz, J$_{5',4}$=3.3 Hz, 1H, H-5'), 3.79 (dd, J$_{5',5}$=11.4 Hz, J$_{5,4}$=3.4 Hz, 1H, H-5), 2.49-2.42 (m, 2H, CH$_2$), 1.68-1.59 (m, 2H, CH$_2$), 1.41-1.30 (m, 2H, CH$_2$), 1.37 and 1.36 (2s, 6H, 2CH$_3$), 0.93 (t, J=7.4 Hz, 3H, CH$_3$). $^{13}$C-NMR (75 MHz, CDCl$_3$) δ 179.1 (C=N), 111.6 (C-6), 86.4 (C-2), 80.4 (C-3), 77.4 (C-4), 62.8 (C-5), 30.8, 28.1, 22.6 (3CH$_2$), 26.8 and 25.6 (2CH$_3$), 13.8 (CH$_3$).

((2S,3R,4R)-1-Octyl-2,3-isopropylidenedioxy-4-hydroxymethyl-pyrroline), colorless crystals, mp 105-6° C. (35%). C$_{16}$H$_{29}$NO$_3$, M=283.21: MS m/z 284.3 (M+H); calcd for C$_{16}$H$_{29}$NO$_3$ (M+H)$^+$ 284.2226, found 284.2227. $^1$H-NMR (400 MHz, CDCl$_3$) δ 4.94 (d, J$_{2,3}$=5.6 Hz, 1H, H-2), 4.58 (d, J$_{3,2}$=5.6 Hz, 1H, H-3), 4.21 (bs, 1H, H-4), 3.88 (dd, J$_{5',5}$=11.4 Hz, J$_{5',4}$=3.3 Hz, 1H, H-5'), 3.78 (dd, J$_{5',5}$=11.4 Hz, J$_{5,4}$=3.4 Hz, 1H, H-5), 2.47-2.41 (m, 2H, CH$_2$), 1.69-1.59 (m, 2H, CH$_2$), 1.36-1.26 (m, 10H, CH$_2$), 1.36 and 1.35 (2s, 6H, 2CH$_3$), 0.87 (t, J=7.0 Hz, 3H, CH$_3$). $^{13}$C-NMR (75 MHz, CDCl$_3$) δ 179.4 (C=N), 111.8 (C-6), 86.6 (C-2), 80.7 (C-3), 77.8 (C-4), 63.0 (C-5), 32.0, 31.4, 29.7, 29.5, 29.4, 27.0, 22.8 (7CH$_2$), 26.8 and 25.6 (2CH$_3$), 14.3 (CH$_3$).

((2S,3R,4R)-1-Nonyl-2,3-isopropylidenedioxy-4-hydroxymethyl-pyrroline), colorless crystals, mp 89-90° C. (39%). C$_{17}$H$_{31}$NO$_3$, M=297.24: MS m/z 298.3 (M+H); calcd for C$_{17}$H$_{31}$NO$_3$ (M+H)$^+$ 298.2382, found 298.2379. $^1$H-NMR (400 MHz, CDCl$_3$) δ 4.95 (d, J$_{2,3}$=5.5 Hz, 1H, H-2), 4.58 (d, J$_{3,2}$=5.5 Hz, 1H, H-3), 4.21 (bs, 1H, H-4), 3.88 (dd, J$_{5',5}$=11.3 Hz, J$_{5',4}$=3.3 Hz, 1H, H-5'), 3.78 (dd, J$_{5',5}$=11.3 Hz, J$_{5,4}$=3.4 Hz, 1H, H-5), 2.48-2.42 (m, 2H, CH$_2$), 1.69-1.61 (m, 2H, CH$_2$), 1.36-1.26 (m, 12H, CH$_2$), 1.36 and 1.35 (2s, 6H, 2CH$_3$), 0.88 (t, J=7.0 Hz, 3H, CH$_3$). $^{13}$C-NMR (75 MHz, CDCl$_3$) δ 179.5 (C=N), 111.8 (C-6), 86.6 (C-2), 80.7 (C-3), 77.8 (C-4), 63.0 (C-5), 32.1, 31.4, 29.8, 29.6, 29.5, 27.1, 22.9 (8CH$_2$), 26.3 and 25.8 (2CH$_3$), 14.3 (CH$_3$).

Step 4: ((1R,2S,3R,4R)-1-R$^1$-2,3-isopropylidenedioxy-4-hydroxymethyl pyrrolidine acetate salt)

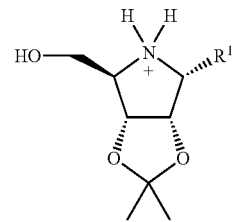

((2S,3R,4R)-1-R$^1$-2,3-Isopropylidenedioxy-4-hydroxymethyl-1-pyrroline (2.5 mmol) in acetic acid (8 ml) was shaken overnight under hydrogen in the presence of 10% palladium-carbon (300 mg) using 50 psi pressures. Thin layer chromatography (TLC) (ethyl acetate: methanol, 4:1) showed complete reactions. The catalyst was removed by filtration through a celite pad and rinsed with acetic acid. Concentration in vacuo and purification of the residue by column chromatography (silica gel, elute with ethyl acetate: methanol, 4:1) afforded ((1R,2S,3R,4R)-1-R$^1$-2,3-isopropylidenedioxy-4-hydroxymethyl pyrrolidine acetate salt as colorless crystalline products. A sample of ((1R,2S,3R,4R)-1-methyl-2,3-isopropylidenedioxy-4-hydroxymethyl pyrrolidine acetate salt was dissolved in aqueous methanol (1:1) and treated with Amberlyst A 21 base resin until the solution had pH 7. The solvent was removed under reduced pressure afforded ((1R,2S,3R,4R)-1-methyl-2,3-isopropylidenedioxy-4-hydroxymethyl pyrrolidine.

((1R,2S,3R,4R)-1-Methyl-2,3-isopropylidenedioxy-4-hydroxymethyl pyrrolidine acetate salt), colorless crystals, mp 93-4° C. (87%). C$_{11}$H$_{21}$NO$_5$, M=247.12; For C$_9$H$_{17}$NO$_3$: MS m/z 188.1 (M+H$^-$); Calcd for C$_9$H$_{17}$NO$_3$ (M+H)$^+$ 188.1287, found 188.1284. $^1$H-NMR (400 MHz, CDCl$_3$) δ 5.29 (bs, NH), 4.57-4.52 (m, 2H, H-2, H-3), 3.66 (dd, J$_{5',5}$=10.8 Hz, J$_{5',4}$=4.0 Hz, 1H, H-5'), 3.44-3.33 (m, 3H, H-5, H-4, H-1), 1.99 (s, 3H, CH$_3$COO$^-$), 1.49 and 1.32 (2s, 6H, 2CH$_3$), 1.26 (d, J=6.7 Hz, 3H, CH$_3$). $^{13}$C-NMR (75 MHz, CDCl$_3$) δ 178.6 (CH$_3$COO$^-$), 111.5 (C-6), 83.9 (C-3), 82.7 (C-2), 66.1 (C-4), 60.4 (C-5), 56.6 (C-1), 26.3 and 24.2 (2CH$_3$), 13.3 (CH$_3$).

((1R,2S,3R,4R)-1-Methyl-2,3-isopropylidenedioxy-4-hydroxymethyl pyrrolidine), C$_9$H$_{17}$NO$_3$, M=187.24. $^1$H-NMR (400 MHz, CDCl$_3$) δ 4.49 (dd, J$_{2,3}$=5.4 Hz, J$_{2,1}$=4.1 Hz, 1H, H-2), 4.38 (d, J$_{3,2}$=5.4 Hz, 1H, H-3), 3.50 (dd, J$_{5',5}$=8.9 Hz, J$_{5',4}$=4.0 Hz, 1H, H-5'), 3.31-3.22 (m, 2H, H-5, H-4), 3.08 (m, 1H, H-1), 2.64 (bs, NH), 1.48 and 1.31 (2s, 6H, 2CH$_3$), 1.22 (d, J=6.6 Hz, 3H, CH$_3$). $^{13}$C-NMR (75 MHz, CDCl$_3$) δ 84.3 (C-3), 83.5 (C-2), 65.9 (C-4), 59.9 (C-5), 55.8 (C-1), 26.4 and 24.2 (2CH$_3$), 13.6 (CH$_3$).

$^1$H-NMR (400 MHz, C$_6$D$_6$) δ 3.92-3.88 (m, 2H, H-2, H-3), 3.29 (dd, J$_{5',5}$=10.3 Hz, J$_{5',4}$=5.7 Hz, 1H, H-5'), 3.18 (dd, $J_{4,5}=10.3$ Hz, $J_{4,5'}=5.7$ Hz, 1H, H-4), 3.18 (t, $J_{5,5'}=10.3$ Hz, $J_{5,4}=10.3$ Hz, 1H, H-4), 2.63 (m, 1H, H-1), 2.35 (bs, NH), 1.35 and 1.13 (2s, 6H, 2CH$_3$), 1.06 (d, 3H, J=6.5 Hz, CH$_3$); $^{13}$C-NMR (75 MHz, C$_6$D$_6$) δ 84.6 (C-3), 83.8 (C-2), 66.7 (C-4), 60.2 (C-5), 56.0 (C-1), 26.7 and 24.4 (2CH$_3$), 13.9 (CH$_3$).

((1R,2S,3R,4R)-1-Butyl-2,3-isopropylidenedioxy-4-hydroxymethyl pyrrolidine acetate salt), colorless crystals, mp 119-120° (90%). C$_{14}$H$_{27}$NO$_5$, M=289.2; For C$_{12}$H$_{23}$NO$_3$: MS m/z 230.2 (M+H). $^1$H-NMR (400 MHz, CDCl$_3$) δ 6.88 (bs, NH), 4.58 (dd, $J_{2,3}=5.5$ Hz, $J_{2,1}=4.1$ Hz, 1H, H-2), 4.48 (d, $J_{3,2}=5.5$ Hz, 1H, H-3), 3.81 (dd, $J_{5',5}=12.0$ Hz, $J_{5',4}=4.0$ Hz, 1H, H-5'), 3.52 (dd, $J_{5',5}=12.0$ Hz, $J_{5,4}=6.5$ Hz, 1H, H-5), 3.47-3.42 (m, 2H, H-4, H-1), 1.99 (s, 3H, CH$_3$COO$^-$), 1.74-1.65 (m, 2H, CH$_2$), 1.45-1.34 (m, 4H, 2CH$_2$), 1.50 and 1.32 (2s, 6H, 2CH$_3$), 0.91 (t, J=7.2 Hz, 3H, CH$_3$). $^{13}$C-NMR (75 MHz, CDCl$_3$) δ 178.6 (CH$_3$COO$^-$), 111.7 (C-6), 83.0 (C-3), 81.2 (C-2), 66.0 (C-4), 61.9 (C-5), 60.4 (C-1), 28.9, 27.9, 22.8 (3CH$_2$), 26.4 and 24.3 (2CH$_3$), 23.7 (CH$_3$COO$^-$), 14.1 (CH$_3$).

((1R,2S,3R,4R)-1-Octyl-2,3-isopropylidenedioxy-4-hydroxymethyl pyrrolidine acetate salt), colorless crystals, mp 95-96° C. (90%). C$_{18}$H$_{31}$NO$_5$, M=345.43; For C$_{16}$H$_{31}$NO$_3$: MS m/z 286.1 (M+H). $^1$H-NMR (400 MHz, CDCl$_3$) δ 5.49 (bs, NH), 4.59 (dd, $J_{2,3}=5.5$ Hz, $J_{2,1}=4.1$ Hz, 1H, H-2), 4.55 (d, $J_{3,2}=5.5$ Hz, 1H, H-3), 3.68 (dd, $J_{5',5}=11.5$ Hz, $J_{5',4}=4.6$ Hz, 1H, H-5'), 3.45 (dd, $J_{5,5'}=11.5$ Hz, $J_{5,4}=7.5$ Hz, 1H, H-5), 3.37 (dd, $J_{4,5}=7.5$ Hz, $J_{4,5'}=4.6$ Hz, 1H, H-4), 3.24 (m, 1H, H-1), 1.97 (s, 3H, CH$_3$COO$^-$), 1.69-1.58 (m, 2H, CH$_2$), 1.48-1.27 (m, 12H, 6CH$_2$), 1.48 and 1.31 (2s, 6H, 2CH$_3$), 0.88 (t, J=7.0 Hz, 3H, CH$_3$). $^{13}$C-NMR (75 MHz, CDCl$_3$) δ 179.1 (CH$_3$COO$^-$), 111.3 (C-6), 83.2 (C-3), 81.4 (C-2), 65.8 (C-4), 61.5 (C-5), 60.3 (C-1), 31.9, 29.8, 29.5, 29.3, 28.4, 26.9, 22.7 (7CH$_2$), 26.2 and 24.1 (2CH$_3$), 14.2 (CH$_3$), −5.3 (2CH$_3$).

((1R,2S,3R,4R)-1-Nonyl-2,3-isopropylidenedioxy-4-hydroxymethyl pyrrolidine acetate salt), colorless crystals, mp 87-88° C. (87%). C$_{19}$H$_{37}$NO$_5$, M=359.45; For C$_{17}$H$_{33}$NO$_3$: MS m/z 300.3 (M+H). $^1$H-NMR (400 MHz, CDCl$_3$) δ 5.39 (bs, NH), 4.57 (dd, $J_{2,3}=5.3$ Hz, $J_{2,1}=4.1$ Hz, 1H, H-2), 4.45 (d, $J_{3,2}=5.3$ Hz, 1H, H-3), 3.64 (dd, $J_{5',5}=11.2$ Hz, $J_{5',4}=4.7$ Hz, 1H, H-5'), 3.41 (dd, $J_{5,5'}=11.2$ Hz, $J_{5,4}=7.8$ Hz, 1H, H-5), 3.33 (dd, $J_{4,5}=7.8$ Hz, $J_{4,5'}=4.7$ Hz, 1H, H-4), 3.18 (m, 1H, H-1), 1.97 (s, 3H, CH$_3$COO$^-$), 1.62 (m, 2H, CH$_2$), 1.47-1.27 (m, 14H, 7CH$_2$), 1.48 and 1.31 (2s, 6H, 2CH$_3$), 0.88 (t, J=7.0 Hz, 3H, CH$_3$); $^{13}$C-NMR (75 MHz, CDCl$_3$) δ 178.9 (CH$_3$COO$^-$), 111.2 (C-6), 83.3 (C-3), 81.6 (C-2), 65.8 (C-4), 61.4 (C-1), 60.3 (C-5), 31.9, 29.8, 29.6, 29.5, 29.4, 28.5, 26.9, 22.7 (8CH$_2$), 26.2 and 24.1 (2CH$_3$), 14.2 (CH$_3$).

Step 5: Synthesis of ((1R,2S,3R,4R)—N—R$^2$-1-R$^1$-2,3-isopropylidenedioxy-4-hydroxymethyl pyrrolidine acetate salt)

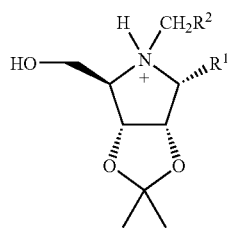

((1R,2S,3R,4R)-1-R$^1$-2,3-Isopropylidenedioxy-4-hydroxymethyl pyrrolidine acetate salt (2 mmol) were treated with nonyl aldehyde (4 mmol, 2 eq) and a catalytic amount of acetic acid in methanol (4 ml) at room temperature (RT) for 1 h under Ar. Then 10% palladium-carbon (200 mg) was added and the reaction mixture was shaken under hydrogen (45 psi). Over night TLC (ethyl acetate) showed complete reactions. The catalyst was removed by filtration through a celite pad and the solvent removed under reduced pressure. The residue was purification by column chromatography (silica gel, elute with ethyl acetate).

((1R,2S,3R,4R)—N-Nonyl-1-methyl-2,3-isopropylidenedioxy-4-hydroxymethyl pyrrolidine acetate salt), as an oil (89%). C$_{20}$H$_{39}$NO$_5$, M=373.27: MS m/z 314.3 (M+H). $^1$H-NMR (400 MHz, CDCl$_3$) δ 4.65 (dd, $J_{3,2}=6.9$ Hz, $J_{3,4}=2.0$ Hz, 1H, H-3), 4.56 (t, $J_{2,3}=6.9$ Hz, 1H, H-2), 3.72 (dd, $J_{5',5}=11.4$ Hz, $J_{5',4}=4.0$ Hz, 1H, H-5'), 3.59 (dd, $J_{5,5'}=11.4$ Hz, $J_{5,4}=3.6$ Hz, 1H, H-5), 3.51 (m, 1H, H-1), 3.13 (bs, 1H, H-4), 2.70-2.58 (m, 2H, CH$_2$), 1.49 and 1.33 (2s, 6H, 2CH$_3$), 1.36-1.28 (m, 14H), 1.10 (d, J=6.8 Hz, 3H, CH$_3$), 0.87 (bt, 3H, CH$_3$); $^{13}$C-NMR (75 MHz, CDCl$_3$) δ 112.5 (C-6), 82.5 (C-3), 80.8 (C-2), 67.2 (C-4), 59.4 (C-5), 58.7 (C-1), 47.2 (CH$_2$), 32.0, 29.8, 29.7, 29.6, 29.4, 28.1, 27.5, 22.8 (CH$_2$), 26.0 and 24.6 (2CH$_3$), 14.3 (CH$_2$CH$_3$), 10.3 (CH$_3$).

((1R,2S,3R,4R)—N-Nonyl-1-butyl-2,3-isopropylidenedioxy-4-hydroxymethyl pyrrolidine acetate salt), as an oil (85%). C$_{23}$H$_{45}$NO$_5$, M=415.56: MS m/z 356.3 (M+H). $^1$H-NMR (400 MHz, CDCl$_3$) δ 4.63 (dd, $J_{2,3}=6.3$ Hz, $J_{2,3}=4.5$ Hz, 1H, H-2), 4.56 (d, $J_{3,2}=6.3$ Hz, 1H, H-3), 3.74-3.66 (m, 1H, H-5'), 3.47 (dd, $J_{5,5'}=11.3$ Hz, $J_{5,4}=6.3$ Hz, 1H, H-5), 3.40 (bt, 1H, H-4), 3.31 (m, 1H, H-1), 2.81 (bt, 2H, CH$_2$), 1.73-1.20 (m, 20H), 1.98 (s, 3H, CH$_3$COO$^-$), 1.49 and 1.31 (2s, 6H, 2CH$_3$), 0.93 (t, J=6.9 Hz, 3H, CH$_3$), 0.87 (t, J=6.5 Hz, 3H, CH$_3$); $^{13}$C-NMR (75 MHz, CDCl$_3$) δ 179.4 (CH$_3$COO$^-$), 111.6 (C-6), 82.4 (C-2), 81.2 (C-3), 69.1 (C-4), 65.3 (C-1), 59.2 (C-5), 48.6, 32.0, 29.7, 29.5, 29.4, 29.1, 28.6, 27.3, 25.5, 23.1, 22.8 (11CH$_2$), 26.3 and 23.9 (2CH$_3$), 14.3 and 14.1 (2CH$_2$CH$_3$)

((1R,2S,3R,4R)—N-Nonyl-1-octhyl-2,3-isopropylidenedioxy-4-hydroxymethyl pyrrolidine acetate salt), as an oil (80%); C$_{23}$H$_{45}$NO$_5$, M=471.67: MS m/z 412.4 (M+H). $^1$H-NMR (400 MHz, CDCl$_3$) δ 4.63 (dd, $J_{2,3}=6.3$ Hz, $J_{2,1}=4.6$ Hz, 1H, H-2), 4.56 (d, $J_{3,2}=6.3$ Hz, 1H, H-3), 3.72 (dd, $J_{5',5}=10.8$ Hz, $J_{5',4}=4.0$ Hz, 1H, H-5'), 3.47-3.40 (m, 2H, H-5, H-4), 3.08 (m, 1H, H-1), 2.84-2.80 (m, 2H, CH$_2$), 1.70-1.67 (m, 2H, CH$_2$), 1.51-1.26 (m, 26H), 1.98 (s, 3H, CH$_3$COO$^-$), 1.49 and 1.31 (2s, 6H, 2CH$_3$), 0.88 (bt, 6H, 2CH$_3$); $^{13}$C-NMR (75 MHz, CDCl$_3$) δ 179.4 (CH$_3$COO$^-$), 111.8 (C-6), 81.4 (C-2), 82.5 (C-3), 69.3 (C-4), 65.2 (C-1), 59.3 (C-5), 48.8, 32.1, 30.0, 29.7, 29.6, 29.4, 28.7, 27.3, 26.9, 25.6, 22.9 (15CH$_2$), 26.4 and 23.9 (2CH$_3$), 14.3 (2CH$_2$CH$_3$)

((1R,2S,3R,4R)—N-Nonyl-1-nonyl-2,3-isopropylidenedioxy-4-hydroxymethyl pyrrolidine acetate salt), as an oil (83%); C$_{28}$H$_{55}$NO$_5$, M=485.69: MS m/z 426.5 (M+H). $^1$H-NMR (400 MHz, CDCl$_3$) δ 4.63 (dd, $J_{2,3}=6.3$ Hz, $J_{2,3}=4.6$ Hz, 1H, H-2), 4.56 (d, $J_{3,2}=6.3$ Hz, 1H, H-3), 3.72 (dd, $J_{5',5}=10.8$ Hz, $J_{5',4}=4.0$ Hz, 1H, H-5'), 3.47-3.40 (m, 2H, H-5, H-4), 3.08 (m, 1H, H-1), 2.84-2.80 (m, 2H, CH$_2$), 1.70-1.67 (m, 2H, CH$_2$), 1.51-1.26 (m, 26H), 1.98 (s, 3H, CH$_3$COO$^-$), 1.49 and 1.31 (2s, 6H, 2CH$_3$), 0.88 (bt, 6H, 2CH$_3$); $^{13}$C-NMR (75 MHz, CDCl$_3$) δ 111.7 (C-6), 81.9 (C-2), 82.7 (C-3), 68.6

(C-4), 64.3 (C-1), 58.8 (C-5), 48.4, 32.1, 30.1, 29.8, 29.6, 29.5, 27.4, 27.2, 25.8, 22.9 (16CH$_2$), 26.5 and 24.1 (2CH$_3$), 14.3 (2CH$_2$CH$_3$)

Step 6: Synthesis of ((1R,2S,3R,4R)-1-R$^1$—N—R$^2$-2,3-diol-4-hydroxymethyl pyrrolidine)

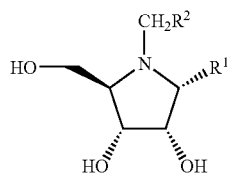

((1R,2S,3R,4R)—N—R$^2$-1-R$^1$-2,3-isopropylidenedioxy-4-hydroxymethyl pyrrolidine acetate salt was dissolved in trifluoroacetic anhydride/water 2:1 (2 ml) at room temperature. The mixture was allowed to stand at room temperature overnight and then evaporated to dryness. Pyrrolidines trifluoroacetate salt were dissolved in aqueous methanol (1:1) and treated with Amberlyst A 21 base resin until the solution had pH 7. The solvent was removed under reduced pressure. The residue was purified by silica gel flash-column, eluting with ethyl acetate/methanol 4:1.

((1R,2S,3R,4R)-1-Methyl-N-nonyl-2,3-diol-4-hydroxymethyl pyrrolidine), colorless oil (98%), C$_{15}$H$_{32}$NO$_3$, M=274.42; MS m/z 274.2 (M); $^1$H-NMR (400 MHz, CDCl$_3$) δ 4.08 (tl, 1H, H-3), 4.02 (t, 1H, H-2), 3.64 (m, 2H, H-5', H-5), 3.46 (m, 1H, H-1), 2.78 (m, 1H, H-4), 2.60-2.43 (m, 2H, CH$_2$), 1.67-1.26 (m, 14H, 7CH$_2$), 1.02 (d, J=6.6 Hz, 3H, CH$_3$), 0.88 (t, J=6.5 Hz, 3H, CH$_3$); $^{13}$C-NMR (75 MHz, CDCl$_3$) δ 74.1 (C-3), 71.9 (C-2), 69.8 (C-4), 60.3 (C-5), 57.8 (C-1), 47.1 (CH$_2$), 32.1, 29.8, 29.5, 28.4, 27.8, 22.9 (7CH$_2$), 14.3 (CH$_3$), 8.4 (CH$_3$).

((1R,2S,3R,4R)-1-Butyl-N-nonyl-2,3-diol-4-hydroxymethyl pyrrolidine), colorless oil (96%), C$_{18}$H$_{37}$NO$_3$, M=315.5; MS m/z 316.4 (M+1); $^1$H-NMR (400 MHz, CDCl$_3$) δ 4.36 (tl, 1H, H-3), 4.15 (tl, 1H, H-2), 3.88 (m, 2H, H-5', H-5), 3.38-3.33 (m, 2H, H-1, H-4), 3.07 (m, 2H, CH$_2$), 1.56-1.26 (m, 30H, 15CH$_2$), 0.88 (2CH$_3$); $^{13}$C-NMR (75 MHz, CDCl$_3$) δ 71.4 (C-3), 71.2 (C-2), 70.9 (C-4), 67.4 (C-1), 58.9 (C-5), 51.8 (CH$_2$), 32.1, 30.3, 29.8, 29.7, 29.5, 29.5, 28.8, 27.8, 27.6, 25.1, 22.9 (14CH$_2$), 14.3 (2CH$_3$).

((1R,2S,3R,4R)-1-Octyl-N-nonyl-2,3-diol-4-hydroxymethyl pyrrolidine), colorless oil (93%). C$_{22}$H$_{45}$NO$_3$, M=371.6; MS m/z 372.4 (M+1). $^1$H-NMR (400 MHz, CDCl$_3$) δ 4.11 (tl, J$_{3,2}$=5.0 Hz, 1H, H-3), 4.01 (tl, 1H, H-2), 3.68 (m, 2H, H-5', H-5), 3.08 (m, 1H, H-1), 2.93 (m, 1H, H-4), 2.68-2.48 (m, 2H, CH$_2$), 1.56-1.26 (m, 30H, 15CH$_2$), 0.88 (2CH$_3$); $^{13}$C-NMR (75 MHz, CDCl$_3$) δ 73.6 (C-3), 72.1 (C-2), 69.4 (C-4), 64.3 (C-1), 60.4 (C-5), 48.7 (CH$_2$), 32.1, 30.3, 29.8, 29.7, 29.5, 29.5, 28.8, 27.8, 27.6, 25.1, 22.9 (14CH$_2$), 14.3 (2CH$_3$).

((1R,2S,3R,4R)-1-Nonyl-N-nonyl-2,3-diol-4-hydroxymethyl pyrrolidine), colorless oil (97%). C$_{23}$H$_{47}$NO$_3$, M=385.63; MS m/z 386.5 (M+H); $^1$H-NMR (400 MHz, CDCl$_3$) δ 4.12 (t, J$_{3,2}$=5.2 Hz, 1H, H-3), 4.02 (dd, J$_{2,3}$=5.2 Hz, J$_{2,1}$=4.8 Hz, 1H, H-2), 3.68 (m, 2H, H-5', H-5), 3.11 (m, 1H, H-1), 2.89 (m, 1H, H-4), 2.71-2.51 (m, 2H, CH$_2$), 1.56-1.26 (m, 32H, 16CH$_2$), 0.88 (2CH$_3$); $^{13}$C-NMR (75 MHz, CDCl$_3$) δ 74.0 (C-3), 72.5 (C-2), 69.3 (C-4), 63.7 (C-1), 60.5 (C-5), 47.9 (CH$_2$), 32.1, 30.3, 29.8, 29.5, 29.0, 28.0, 27.6, 25.1, 22.9 (15CH$_2$), 14.3 (2CH$_3$).

Example 2

Preparation of ((1S,2R,3S,4S)-1-R$^1$—N—R$^2$-2,3-diol-4-hydroxymethyl pyrrolidine)

Step 1: Synthesis of 5-O-methanesulfonyl-2,3-O-isopropylidene-D-lyxonolactone

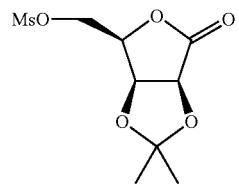 [SMILES: CC1(C)O[C@@H]2[C@H](O1)C(=O)O[C@@H]2COS(C)(=O)=O]

2,3-O-Isopropylidene-D-lyxonolactone (5 g, 26.6 mmol) was dissolved in pyridine (8 ml) and methanesulfonylchloride (2 ml, 29.2 mmol, 1.1 eq) was added to a stirred at 0° C. over 10 min. The mixture was kept at 0° C. for 1 h. 0.5 ml water was then added and the mixture was extracted with methylene chloride (15 ml). The extract was washed with HCl 10% (2×5 ml) and with aqueous NaHCO$_3$ (5 ml). The organic phase was dried (MgSO$_4$), filtered and evaporated under reduced pressure to yield 5-O-methanesulfonyl-2,3-O-isopropylidene-D-lyxonolactone (95%) as colorless crystals.

$^1$H-NMR (400 MHz, CDCl$_3$) δ 4.89 (d, 2H, H-2, H-3), 4.79 (m, 1H, H-4), 4.56 (dd, J$_{5',5}$=11.7 Hz, J$_{5',4}$=4.1 Hz, 1H, H-5'), 4.48 (dd, J$_{5,5'}$=11.7 Hz, J$_{5,4}$=7.6 Hz, 1H, H-5), 3.11 (s, 3H, CH$_3$SO$_2$), 1.49 and 1.40 (2s, 6H, 2CH$_3$); $^{13}$C-NMR (75 MHz, CDCl$_3$) δ 172.9 (CO), 115.1 (C-6), 76.4 (C-2), 76.0 (C-4), 75.6 (C-3), 67.1 (C-5), 37.9 (CH$_3$SO$_2$), 26.9 and 25.9 (2CH$_3$).

Details of synthesis 5-O-methanesulfonyl-2,3-O-isopropylidene-D-lyxonolactone can be also found in (a) Fleet G. W. J.; Ramsden N. G.; Witty D. R. *Tetrahedron* 1989, 45(1), 319. (b) Fleet G. W. J.; Petursson S.; Campbell A. L.; Mueller R. A.; Behling J. R.; Babiak K. A.; Ng J. S; Scaros M. G.; *J. Chem. Soc. Perkin Trans* 1, 1989, 665. (c) Han S.-Y.; Joullié M. M.; Fokin V. V.; Petasis N. A. *Tetrahedron: Asymmetry* 1997, 3(12), 2535. (d) Gogskesen M.; Lundt I.; Søtofte I. *Tetrahedron: Asymmetry* 2000, 11, 567, all incorporated herein by reference.

Step 2: Synthesis of 1-R-5-O-methanesulfonyl-2,3-O-isopropylidene-D-lyxose

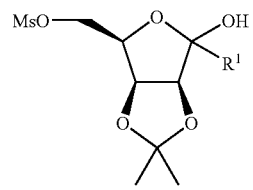

5-O-Methanesulfonyl-2,3-O-isopropylidene-D-lyxono-1,4-lactone (5 g, 18 mmol) was dissolved in THF (125 ml) anhydrous under Ar. The solution was cooled to −68° C., maintaining the temperature between −50° C.~−40° C., the Grignard reagent (1.5 eq) was added with stirred over 20 min. The temperature was allowed to warm to 0° C. and the solution was stirred 1 h. After quenching with saturated aqueous NH$_4$Cl, the mixture was extracted with ethyl acetate (2×15 ml). The combined extracts were washed with saturated aqueous NH$_4$Cl, dried over Na$_2$SO$_4$, and filtered. Evaporation of the filtrate under vacuo afforded 1-R$^1$-5-O-methanesulfonyl-2,3-O-isopropylidene-D-lyxoses as a stereoisomer mixture at the anomeric carbon atom.

1-Nonyl-5-O-methanesulfonyl-2,3-O-isopropylidene-D-lyxose, (94%) colorless oil. Ratio of isomers α:β~22:78. C$_{18}$H$_{34}$O$_7$S, M=394.53. $^1$H-NMR (400 MHz, CDCl$_3$) δβ:4.82 (dd, J$_{3,2}$=5.8 Hz, J$_{3,4}$=3.4 Hz, 1H, H-3), 4.49 (dd, J$_{5',5}$=8.3 Hz, J$_{5',4}$=1.5 Hz, 1H, H-5), 4.47 (d, J$_{2,3=5.8}$ Hz, 1H, H-2), 4.40-4.33 (m, 2H, H-4, H-5), 3.06 (s, 3H, CH$_3$SO$_2$), 1.88-1.68 (m, 2H, CH$_2$), 1.45 and 1.30 (2s, 6H, 2CH$_3$), 1.45-1.24 (m, 14H, CH$_2$), 0.88 (tl, 3H, CH$_3$); α: 4.78 (dd, J$_{3,2}$=6.0 Hz, J$_{3,4}$=3.9 Hz, H-3), 4.52-4.43 (m, H-5'), 4.40-4.33 (m, 2H, H-2, H-5), 3.93 (m, 1H, H-4), 3.07 (s, 3H, CH$_3$SO$_2$), 1.54 and 1.36 (2s, 6H, 2CH$_3$); $^{13}$C-NMR (75 MHz, CDCl$_3$) δβ: 112.8 (C-6), 107.2 (C-1), 84.5 (C-2), 80.1 (C-3), 76.3 (C-4), 68.4 (C-5), 37.4 (CH$_3$SO$_2$), 35.1, 31.8, 29.7, 29.5, 29.4, 29.3, 23.2, 22.6 (8CH$_2$), 25.9 and 25.8 (2CH$_3$), 14.1 (CH$_3$); α: 113.6 (C-6), 104.6 (C-1), 79.7 (C-3), 73.8 (C-4), 68.2 (C-5), 37.5 (CH$_3$SO$_2$), 25.8 and 24.6 (2CH$_3$), 14.1 (CH$_3$).

Step 3: Synthesis of (2R,3S,4S)-1-R$^1$-2,3-isopropylidenedioxy-4-hydroxymethyl-1-pyrrolin

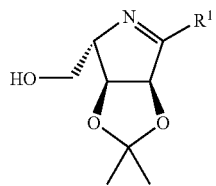

1-R-5-O-Methanesulfonyl-2,3-O-isopropylidene-D-lyxose (14 mmol) was dissolved in NH$_3$/EtOH 3:1 (50 ml). The solution was allowed to stand 2 days at room temperature in a sealed flask. The solvent was removed under reduced pressure, and the residue was dissolved in methanol (5 ml) and dried over Na$_2$SO$_4$, and filtered. Evaporation of the filtrate under vacuo afforded the crude product which was purified by silica gel column chromatography, eluting with ethyl acetate, to afford (2R,3S,4S)-1-R$^1$-2,3-isopropylidenedioxy-4-hydroxymethyl-1-pyrrolines as colorless crystalline products.

(2R,3S,4S)-1-Nonyl-2,3-isopropylidenedioxy-4-hydroxymethyl-1-pyrroline), colorless crystals, mp 89-90° C. (39%). C$_{17}$H$_{31}$NO$_3$, M=297.24: MS m/z 298.3 (M+H); calcd for C$_{17}$H$_{31}$NO$_3$ (M+H)$^+$298.2382, found 298.2379. $^1$H-NMR (400 MHz, CDCl$_3$) δ 4.95 (d, J$_{2,3}$=5.5 Hz, 1H, H-2), 4.58 (d, J$_{3,2}$=5.5 Hz, 1H, H-3), 4.21 (bs, 1H, H-4), 3.88 (dd, J$_{5',5}$=11.3 Hz, J$_{5',4}$=3.3 Hz, 1H, H-5'), 3.78 (dd, J$_{5',5}$=11.3 Hz, J$_{5,4}$=3.4 Hz, 1H, H-5), 2.48-2.42 (m, 2H, CH$_2$), 1.69-1.61 (m, 2H, CH$_2$), 1.36-1.26 (m, 12H, CH$_2$), 1.36 and 1.35 (2s, 6H, 2CH$_3$), 0.88 (t, J=7.0 Hz, 3H, CH$_3$). $^{13}$C-NMR (75 MHz, CDCl$_3$) δ 179.5 (C=N), 111.8 (C-6), 86.6 (C-2), 80.7 (C-3), 77.8 (C-4), 63.0 (C-5), 32.1, 31.4, 29.8, 29.6, 29.5, 27.1, 22.9 (8CH$_2$), 26.3 and 25.8 (2CH$_3$), 14.3 (CH$_3$).

Step 4: Synthesis of (1S,2R,3S,4S)-1-R$^1$-2,3-isopropylidenedioxy-4-hydroxymethyl pyrrolidine acetate salt

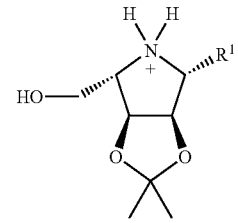

(2R,3S,4S)-1-R$^1$-2,3-Isopropylidenedioxy-4-hydroxymethyl-1-pyrroline (2.5 mmol) in acetic acid (8 ml) was shaken overnight under hydrogen in the presence of 10% palladium-carbon (300 mg) using 50 psi pressures. TLC (ethyl acetate: methanol, 4:1) showed complete reactions. The catalyst was removed by filtration through a celite pad and rinsed with acetic acid. Concentration in vacuo and purification of the residue by column chromatography (silica gel, elute with ethyl acetate: methanol, 4:1) afforded (1S,2R,3S,4S)-1-R$^1$-2,3-isopropylidenedioxy-4-hydroxymethyl pyrrolidine acetate salt as colorless crystalline products.

(1S,2R,3S,4S)-1-Nonyl-2,3-isopropylidenedioxy-4-hydroxymethyl pyrrolidine acetate salt, colorless crystals, mp 87-88° C. (90%). C$_{19}$H$_{37}$NO$_5$, M=359.45; For C$_{17}$H$_{33}$NO$_3$: MS m/z 300.3 (M+H). $^1$H-NMR (400 MHz, CDCl$_3$) δ 5.39 (bs, NH), 4.57 (dd, J$_{2,3}$=5.3 Hz, J$_{2,3}$=4.1 Hz, 1H, H-2), 4.45 (d, J$_{3,2}$=5.3 Hz, 1H, H-3), 3.64 (dd, J$_{5',5}$=11.2 Hz, J$_{5',4}$=4.7 Hz, 1H, H-5'), 3.41 (dd, J$_{5,5'}$=11.2 Hz, J$_{5,4}$=7.8 Hz, 1H, H-5), 3.33 (dd, J$_{4,5}$=7.8 Hz, J$_{4,5'}$=4.7 Hz, 1H, H-4), 3.18 (m, 1H, H-1), 1.97 (s, 3H, CH$_3$COO$^-$), 1.62 (m, 2H, CH$_2$), 1.47-1.27 (m, 14H, 7CH$_2$), 1.48 and 1.31 (2s, 6H, 2CH$_3$), 0.88 (t, J=7.0 Hz, 3H, CH$_3$); $^{13}$C-NMR (75 MHz, CDCl$_3$) δ 178.9 (CH$_3$COO$^-$), 111.2 (C-6), 83.3 (C-3), 81.6 (C-2), 65.8 (C-4), 61.4 (C-1), 60.3 (C-5), 31.9, 29.8, 29.6, 29.5, 29.4, 28.5, 26.9, 22.7 (8CH$_2$), 26.2 and 24.1 (2CH$_3$), 14.2 (CH$_3$).

Step 5: Synthesis of (1S,2R,3S,4S)—N—R$^2$-1-R$^1$-2,3-isopropylidenedioxy-4-hydroxymethyl pyrrolidine acetate salt

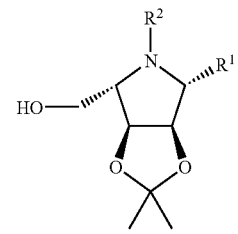

(1S,2R,3S,4S)-1-R$^1$-2,3-Isopropylidenedioxy-4-hydroxymethyl pyrrolidine acetate salt (2 mmol) were treated with nonyl aldehyde (4 mmol, 2 eq) and a catalytic amount of acetic acid in methanol (4 ml) at RT for 1 h under Ar. Then 10% palladium-carbon (200 mg) was added and the reaction mixture was shaken under hydrogen (45 psi). Over night TLC (ethyl acetate) showed complete reactions. The catalyst was removed by filtration through a celite pad and the solvent removed under reduced pressure. The residue was purification by column chromatography (silica gel, elute with ethyl acetate).

(1S,2R,3S,4S)—N-Nonyl-1-nonyl-2,3-isopropylidenedioxy-4-hydroxymethyl pyrrolidine acetate salt), as an oil (83%); $C_{28}H_{55}NO_5$, M=485.69: MS m/z 426.5 (M+H). $^1$H-NMR (400 MHz, CDCl$_3$) δ 4.63 (dd, $J_{2,3}$=6.3 Hz, $J_{2,1}$=4.6 Hz, 1H, H-2), 4.56 (d, $J_{3,2}$=6.3 Hz, 1H, H-3), 3.72 (dd, $J_{5',5}$=10.8 Hz, $J_{5',4}$=4.0 Hz, 1H, H-5'), 3.47-3.40 (m, 2H, H-5, H-4), 3.08 (m, 1H, H-1), 2.84-2.80 (m, 2H, CH$_2$), 1.70-1.67 (m, 2H, CH$_2$), 1.51-1.26 (m, 26H), 1.98 (s, 3H, CH$_3$COO$^-$), 1.49 and 1.31 (2s, 6H, 2CH$_3$), 0.88 (bt, 6H, 2CH$_3$); $^{13}$C-NMR (75 MHz, CDCl$_3$) δ 111.7 (C-6), 81.9 (C-2), 82.7 (C-3), 68.6 (C-4), 64.3 (C-1), 58.8 (C-5), 48.4, 32.1, 30.1, 29.8, 29.6, 29.5, 27.4, 27.2, 25.8, 22.9 (16CH$_2$), 26.5 and 24.1 (2CH$_3$), 14.3 (2CH$_2$CH$_3$)

Step 6: Synthesis of (1S,2R,3S,4S)-1-nonyl-2,3-diol-4-hydroxymethyl pyrrolidine trifluoroacetate salt

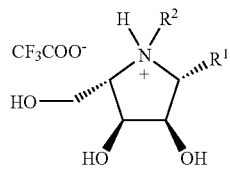

(1S,2R,3S,4S)—N—R$^2$-1-R$^1$-2,3-isopropylidenedioxy-4-hydroxymethyl pyrrolidine acetate salt was dissolved in trifluoroacetic anhydride/water 2:1 (2 ml) at room temperature. The mixture was allowed to stand at room temperature overnight and then evaporated to dryness. The residue was purified by silica gel flash-column, eluting with ethyl acetate/methanol 4:1.

(1S,2R,3S,4S)-1-Decyl-2,3-diol-4-hydroxymethyl pyrrolidine trifluoroacetate salt, colorless crystals, mp 114-5° C. (92%). $C_{17}F_3H_{32}NO_5$, M=387.2; For $C_{15}H_{31}NO_3$: MS m/z 274.2 (M+H)$^+$: Mass spectrum calculated for $C_{15}H_{31}NO_3$ (M+H)$^+$ 274.2382, found 274.2384. $^1$H-NMR (400 MHz, CD$_3$OD) δ 4.14 (dd, $J_{3,4}$=8.8 Hz, $J_{3,2}$=3.6 Hz, 1H, H-3), 4.05 (dd, $J_{2,3}$=3.6 Hz, $J_{2,1}$=2.8 Hz, 1H, H-2), 3.85 (dd, $J_{5',5}$=11.9 Hz, $J_{5',4}$=3.1 Hz, 1H, H-5'), 3.80 (dd, $J_{5,5'}$=11.9 Hz, $J_{5,4}$=5.6 Hz, 1H, H-5), 3.43 (m, 2H, H-1, H-4); 1.87-1.61 (m, 2H, CH$_2$); 1.34-126 (m, 16H, CH$_2$); 0.87 (t, J=6.5 Hz, 3H, CH$_3$); $^{13}$C-NMR (75 MHz, CD$_3$OD) δ 73.4 (C-3), 72.1 (C-2), 63.9, 63.3 (C-4, C-1), 59.8 (C-5), 33.2, 30.9, 30.8, 30.7, 30.6, 27.9, 27.2 (9CH$_2$) 14.6 (CH$_3$).

(1S,2R,3S,4S)-1-Nonyl-N-nonyl-2,3-diol-4-hydroxymethyl pyrrolidine trifluoroacetate salt, semi crystalline solid (87%). $C_{25}F_3H_{48}NO_5$, M=499.6; For $C_{23}H_{47}NO_3$: MS m/z 386.5 (M+1). $^1$H-NMR (400 MHz, CDCl$_3$) δ 4.45 (sl, 1H, H-3), 4.18 (sl, 1H, H-2), 3.91 (m, 2H, H-5', H-5), 3.48 (m, 1H, H-1, H-1), 3.41 (m, 1H, H-1, H-4), 3.20 (m, 2H, CH$_2$), 1.96-1.26 (m, 32H, 16CH$_2$), 0.88 (2CH$_3$). $^{13}$C-NMR (75 MHz, CDCl$_3$) δ 72.7 (C-4), 71.1, 70.9 (C-2, C-3), 68.4 (C-1), 59.1 (C-5), 53.6 (CH$_2$), 32.0, 31.9, 29.6, 29.5, 29.3, 26.8, 26.5, 25.5, 24.4, 22.8 (15CH$_2$), 14.3 (2CH$_3$).

Step 7: Synthesis of (1S,2R,3S,4S)-1-Nonyl-N-nonyl-2,3-diol-4-hydroxymethyl pyrrolidine

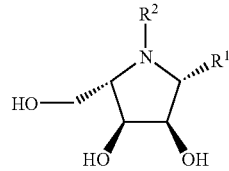

Pyrrolidines trifluoroacetate salt were dissolved in aqueous methanol (1:1) and treated with Amberlyst A 21 base resin until the solution had pH 7. The solvent was removed under reduced pressure afforded (1S,2R,3S,4S)-1-nonyl-N-nonyl-2,3-diol-4-hydroxymethyl pyrrolidine, colorless oil (96%).

$C_{23}H_{47}NO_3$, M=385.63; MS m/z 386.5 (M+H). $^1$H-NMR (400 MHz, CDCl$_3$) δ 4.08 (t, $J_{3,2}$=5.2 Hz, 1H, H-3), 4.0 (dd, $J_{2,3}$=5.2 Hz, $J_{2,1}$=4.8 Hz, 1H, H-2), 3.66 (d, 2H, H-5', H-5), 3.08 (m, 1H, H-1), 2.87 (m, 1H, H-4), 2.68-2.48 (m, 2H, CH$_2$), 1.56-1.26 (m, 32H, 16CH$_2$), 0.88 (2CH$_3$). $^{13}$C-NMR (75 MHz, CDCl$_3$) δ 72.7 (C-3), 71.1 (C-2), 70.9 (C-4), 68.4 (C-1), 59.0 (C-5), 53.6 (CH$_2$), 32.1, 30.4, 29.8, 29.5, 29.3, 28.1, 27.7, 25.1, 22.9 (15CH$_2$), 14.3 (2CH$_3$).

Example 3

(1S,2R,3S,4S,5R)-1-octhyl-2,3-diol-5,6-dihydroxyethyl pyrrolidine trifluoroacetate salt Step 1: Synthesis of 2,3-O-Isopropylidene-6-O-triphenylmethyl-D-mannono-1,4-lactone

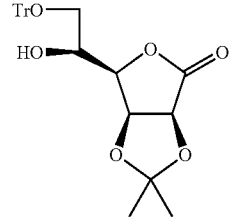

2,3-O-isopropilidene-D-mannono-1,4-lactone was prepared from D-mannose (Sigma Aldrich) using known procedure, see. e.g. (a) Vonlanthen D.; Leumann C. J. *Synthesis* 2003, 7, 1087-90. (b) Manna S.; McAnalley B. H.; Ammon H. L. *Carbohydr. Res.* 1993, 243, 11-27. (c) Goodyear E. H.; Haworth W. N. *J. Chem. Soc.* 1927, 3136-3146. (d) Ohle H.; Berend G. *Chem. Ber.* 1925, 58, 2590-2592. (e) Tam T. F.; Fraser-Reid B. *J. Org. Chem.* 1980, 45, 1344-1346. (f) Joseph C. C.; Regeling H.; Zwanenburg B.; Chittenden G. J. F. *Tetrahedron* 2002, 58, 6907, all incorporated herein by reference in their entirety. A solution of 2,3-O-isopropilidene-D-mannono-1,4-lactone (3.55 g, 16.3 mmol) and triphenylmethyl chloride (6.34 g, 22.7 mmol, 1.4 eq) in pyridine (60 ml) was stirred for 24 h. The pyridine was removed under reduced pressure, and the residue was purified by silica gel column chromatography, eluting with ethyl acetate:xexane 1:2, to afford 2,3-O-isopropylidene-6-O-triphenylmethyl-D-mannono-1,4-lactone (68%) as a white crystalline solid, m.p. 68-69° C. $C_{28}H_{28}O_6$, M=460.53: MS m/z 483.7 (M+Na)$^+$; Calcd for $C_{28}H_{28}O_6$ (M+Na)+483.1784, found 483.1797; $^1$H-NMR (400 MHz, CDCl$_3$) δ 7.44 (d, 6H, 3 Ph, H-2'; H-6'), 7.31 (t, 6H, H-3', H-5'), 7.24 (t, 3H, H-4'), 4.90 (dd, 1H, $J_{3,2}$=5.3 Hz, $J_{3,4}$=3.5 Hz, H-3); 4.79 (d, 1H, $J_{3,2}$=5.3 Hz, H-2); 4.47 (dd, 1H, $J_{4,5}$=8.4 Hz, $J_{4,3}$=3.5 Hz, H-4); 4.09-4.06 (m, 1H, H-5); 3.50 (dd, $J_{6',6}$=10.0 Hz, $J_{6',5}$=3.4 Hz, 1H, H-6'), 3.40 (dd, $J_{6,6'}$=10.0, $J_{6,5}$=4.9 Hz, 1H, H-6); 1.41 and 1.46 (2s, 6H, 2CH$_3$); $^{13}$C-NMR (75 MHz, CDCl$_3$) δ 173.7 (CO), 143.7 (C-1'), 128.2, 128.7 (C-2', C-3'), 127.5 (C-4'), 114.5 (C(CH$_3$)$_2$), 87.3 (CPh$_3$), 77.5 (H-4), 76.6 (H-3), 76.2 (H-2), 68.7 (H-5), 64.5 (H-6), 26.2 and 27.0 (2CH$_3$).

Step 2: Synthesis of 2,3-O-Isopropylidene-5-O-methanesulfonyl-6-O-triphenylmethyl-D-mannono-1,4-lactone

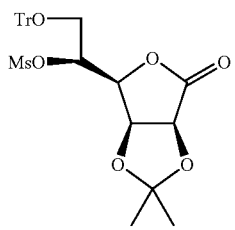

2,3-O-Isopropylidene-6-O-triphenylmethyl-D-mannono-1,4-lactone (3 g, 6.5 mmol) was dissolved in pyridine (6 ml) and methanesulfonylchloride (1 ml, 13 mmoli, 2 eq) was added to a stirred at 0° C. over 10 min. The mixture was kept at 0° C. for 5 h. 0.5 ml water was then added and the mixture was extracted with methylene chloride. The extract was washed with HCl 10% and with aqueous NaHCO$_3$. The organic phase was dried (MgSO$_4$), filtered and evaporated under reduced pressure to yield 2,3-O-isopropylidene-5-O-methanesulfonyl-6-O-triphenylmethyl-D-mannono-1,4-lactone (98%) as colorless crystals, m.p. 90-91° C.

$^1$H-NMR (400 MHz, CDCl$_3$) δ 7.44 (d, 6H, 3Ph, H-2'; H-6'), 7.31 (t, 6H, 3Ph H-3', H-5'), 7.24 (t, 3H, 3Ph, H-4'), 5.01 (m, $J_{5,4}$=7.5 Hz, $J_{5,6}$=4.5 Hz, $J_{5,6'}$=2.1 Hz, 1H, H-5), 4.90-4.86 (m, 2H, H-3, H-4), 4.80 (d, $J_{2,3}$=5.0 Hz, 1H, H-2), 3.72 (dd, $J_{6',6}$=11.3 Hz, $J_{6',5=2.1}$ Hz, 1H, H-6'), 3.40 (dd, $J_{6,6'}$=11.3 Hz, $J_{6,5}$=4.5 Hz, 1H, H-6), 3.02 (s, 3H, CH$_3$SO$_2$), 1.36 and 1.37 (2s, 6H, 2CH$_3$); $^{13}$C-NMR (75 MHz, CDCl$_3$) δ 172.8 (CO), 143.3 (C-1'), 128.2, 128.8 (C-2', C-3'), 127.5 (C-4'), 114.7 (C(CH$_3$)$_2$), 87.3 (CPh$_3$), 77.8 (H-5), 76.0 (H-2), 75.6 (H-4), 75.5 (H-3), 62.5 (H-6), 39.0 (CH$_3$SO$_2$), 26.1 and 26.9 (2CH$_3$).

Step 3: Synthesis of 1-Methyl-2,3-O-isopropylidene-5-O-methanesulfonyl-6-O-triphenylmethyl-D-mannose

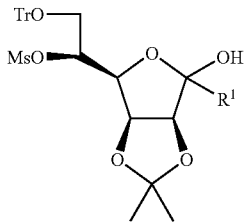

2,3-O-Isopropylidene-5-O-methanesulfonyl-6-O-triphenylmethyl-D-mannono-1,4-lactone (3.2 g, 6 mmol) was dissolved in THF (40 ml) anhydrous under Ar. The solution was cooled to −68° C., maintaining the temperature between −50° C.~−40° C., the Grignard reagent (3 ml, 8.9 mmol, 1.5 eq) was added with stirred over 20 min. The temperature was allowed to warm to 0° C. and the solution was stirred 2 h. After quenching with saturated aqueous NH$_4$Cl, the mixture was extracted with ethyl acetate. The combined extracts were washed with saturated aqueous NH$_4$Cl, dried over Na$_2$SO$_4$, and filtered. Evaporation of the filtrate under vacuo afforded 1-methyl-2,3-O-isopropylidene-5-O-methanesulfonyl-6-O-triphenylmethyl-D-mannose (99%) as a colorless oil.

$^1$H-NMR (500 MHz, CDCl$_3$) δ 7.46 (d, 6H, 3Ph, H-2'; H-6'), 7.29 (t, 6H, 3Ph, H-3', H-5'); 7.22 (t, 3H, 3Ph, H-4'); 4.99 (m, 1H, $J_{5,4}$=7.6 Hz, $J_{5,6}$=5.1, $J_{5,6'}$=2.1, H-5), 4.82 (dd, 1H, $J_{3,2}$=5.8, Hz, $J_{3,4}$=3.8 Hz, H-3); 4.45 (dd, 1H, $J_{4,5}$=7.6, Hz, $J_{4,3}$=3.8 Hz, H-4); 4.42 (d, 1H, $J_{2,3}$=5.8, H-2); 3.67 (dd, 1H, $J_{6',6}$=11.1 Hz, $J_{6',5}$=2.1 Hz, H-6'), 3.36 (dd, 1H, $J_{6,6'}$=11.1 Hz, $J_{6,5=5.1}$ Hz, H-6), 3.02 (s, 3H, CH$_3$SO$_2$); 1.37 (s, 3H, CH$_3$); 1.28 and 1.31 (2s, 6H, 2CH$_3$); $^{13}$C-NMR (75 MHz, CDCl$_3$) δ 143.8 (C-1'), 128.9 and 127.9 (C-2' and C-3'), 127.2 (C-4'), 112.9 (C(CH$_3$)$_2$), 105.3 (C-1), 86.9 (CPh$_3$), 85.4 (H-2), 80.3 (H-3), 79.5 (H-5), 76.6 (H-4), 63.1 (H-6), 39.0 (CH$_3$SO$_2$), 26.8 and 25.7 (2CH$_3$), 22.3 (CH$_3$).

Step 4: Synthesis of (2R,3S,4S,5R)-1-methyl-2,3-isopropylidenedioxy-6-O-triphenylmethyl-5,6-hydroxyethyl-1-pyrroline

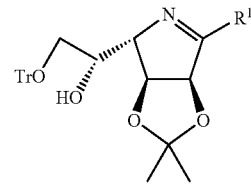

1-Methyl-2,3-O-isopropylidene-5-O-methanesulfonyl-6-O-triphenylmethyl-D-mannose (3 g, 5.4 mmol) was dissolved in NH$_3$/EtOH 2:1 (50 ml). The solution was allowed to stand 4 days at room temperature in a sealed flask. The solvent was removed under reduced pressure, and the residue was dissolved in methanol and dried over Na$_2$SO$_4$, and filtered. Evaporation of the filtrate under vacuo afforded the crude product which was purified by silica gel column chromatography, eluting with ethyl acetate, to afford ((2R,3S,4S,5R)-1-methyl-2,3-isopropylidenedioxy-6-O-triphenylmethyl-5,6-hydroxyethyl-1-pyrroline (42%) as colorless crystalline products, m.p. 85° C.

$C_{29}H_{31}NO_4$, M=457.57: MS m/z 480.3 (M+Na); Calcd for $C_{29}H_{31}NO_4$ (M+Na) 480.2151, found 480.2142; $^1$H-NMR (400 MHz, CDCl$_3$) δ 7.44 (d, 6H, 3Ph, H-2'; H-6'), 7.30 (t, 6H, 3Ph, H-3', H-5'); 7.23 (t, 3H, 3Ph, H-4'); 4.81 (s, $J_{3,2}$=5.6 Hz, 1H, H-3); 4.58 (s, $J_{2,3}$=5.6 Hz, 1H, H-2), 4.19 (s, 1H, H-4), 3.96 (m, 1H, H-5), 3.35 (dd, $J_{6',6}$=9.5 Hz, $J_{6',5}$=7.1 Hz, 1H, H-6'), 3.27 (dd, $J_{6,6'}$=9.5 Hz, $J_{6,5}$=3.5 Hz, 1H, H-6), 2.06 (s, 3H, CH$_3$), 1.33 and 1.32 (2s, 6H, 2CH$_3$); $^{13}$C-NMR (75 MHz, CDCl$_3$) δ 175.5 (C=N), 143.8 (C-1'), 128.9, 127.9

(C-2', C-3'), 127.2 (C-4'), 111.7 (C-7), 87.5 (H-3), 87.3 (CPh$_3$), 78.9, 78.7 (H-2, H-4), 70.6 (H-5), 65.7 (H-6), 27.1 and 25.9 (2CH$_3$), 17.2 (CH$_3$).

Step 5: Synthesis of (1S,2R,3S,4S,5R)-1-methyl-2,3-isopropylidenedioxy-6-O-triphenylmethyl-5,6-dihydroxyethyl pyrrolidine acetate salt

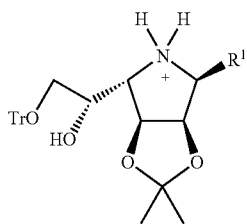

A solution of ((2R,3S,4S,5R)-1-methyl-2,3-isopropylidenedioxy-6-O-triphenylmethyl-5,6-hydroxyethyl-1-pyrroline (1 g, 2.1 mmol) in acetic acid (8 ml) was shaken overnight under hydrogen in the presence of 10% palladium-carbon (300 mg) using 50 psi pressures. TLC (ethyl acetate: methanol, 4:1) showed complete reactions. The catalyst was removed by filtration through a celite pad and rinsed with acetic acid. Concentration in vacuo and purification of the residue by column chromatography (silica gel, elute with ethyl acetate/methanol 4:1) afforded ((1S,2R,3S,4S,5R)-1-methyl-2,3-isopropylidenedioxy-6-O-triphenylmethyl-5,6-dihydroxyethyl pyrrolidine acetate salt (85%) as a colorless crystals, mp 167-170° C. C$_{31}$H$_{37}$NO$_6$, M=459.58; MS m/z 482.3 (M+Na); $^1$H-NMR (400 MHz, CDCl$_3$) δ 7.42 (d, 6H, 3Ph, H-2', H-6'), 7.29-7.19 (m, 9H, 3Ph, H-3', H-4', H-5'), 4.82 (d, J$_{3,2}$=5.7 Hz, 1H, H-3), 4.82 (d, J$_{2,3}$=5.7 Hz, J$_{2,1}$=4.8 Hz, 1H, H-2), 4.10 (m, 1H, H-5), 3.73-3.66 (m, 2H, H-1, H-4), 3.30 (dd, 1H, J$_{6',6}$=9.5 Hz, J$_{6,5}$=6.1 Hz, 1H, H-6'), 3.19 (t, J$_{6,6'}$=9.5 Hz, J$_{6,5}$=7.4 Hz, 1H, H-6), 2.0 (2, 3H, CH$_3$COO$^-$), 1.50 and 1.31 (2s, 6H, 2CH$_3$), 1.25 (d, J=6.6 Hz, 3H, CH$_3$); $^{13}$C-NMR (75 MHz, CDCl$_3$) δ 178.1 (CH$_3$COO$^-$), 143.7 (C-1'), 128.9, 128.0 (C-2', C-3'), 127.3 (C-4'), 111.4 (C-7), 87.2 (CPh$_3$), 81.9 (C-2, C-3), 69.1 (C-5), 66.8 (C-4), 64.6 (C-6), 58.1 (C-1), 26.4 and 24.2 (2CH$_3$), 23.3 (CH$_3$COO$^-$), 13.3 (CH$_3$).

Step 6: Synthesis of (1S,2R,3S,4S,5R)-1-methyl-N-nonyl-2,3-isopropylidenedioxy-6-O-triphenylmethyl-5,6-dihydroxyethyl pyrrolidine acetate salt

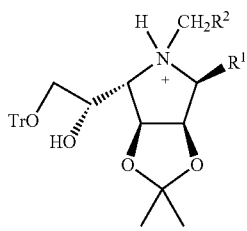

((1S,2R,3S,4S,5R)-1-Methyl-2,3-isopropylidenedioxy-6-O-triphenylmethyl-5,6-dihydroxyethyl pyrrolidine acetate salt (0.95 g, 1.8 mmol) were treated with nonyl aldehyde (0.6 ml, 3.6 mmol, 2 eq) and acetic acid (0.1 ml) in methanol (4 ml) at RT for 1 h under Ar. Then 10% palladium-carbon (100 mg) was added and the reaction mixture was shaken under hydrogen (45 psi). Over night TLC (ethyl acetate) showed complete reactions. The catalyst was removed by filtration through a celite pad and the solvent removed under reduced pressure. Purification by flash chromatography (ethyl acetate) afforded ((1S,2R,3S,4S,5R)-1-methyl-N-nonyl-2,3-isopropylidenedioxy-6-O-triphenylmethyl-5,6-dihydroxyethyl pyrrolidine acetate salt (80%) as an colorless oil. C$_{40}$H$_{55}$NO$_6$, M=646.4; For C$_{38}$H$_{51}$NO$_4$: MS m/z 586.4 (M+H); $^1$H-NMR (400 MHz, CDCl$_3$) δ 7.42 (d, 6H, 3Ph, H-2', H-6'), 7.30-7.24 (m, 9H, 3Ph, H-3', H-4', H-5'); 4.74 (d, J$_{3,2}$=5.2 Hz, 1H, H-3), 4.49 (dd, J$_{2,3}$=5.2, J$_{2,1}$=4.1 Hz, 1H, H-2), 4.34 (m, 1H, H-5), 4.23 (m, 1H, H-1), 4.05 (s, 1H, H-4), 3.32 (dd, J$_{6',6}$=7.5 Hz, J$_{6',5}$=4.4 Hz, 1H, H-6'), 3.16 (t, J$_{6',6}$=7.5 Hz, 1H, H-6'), 3.09-2.94 (m, 2H, CH$_2$), 2.27 (m, 2H, CH$_2$), 1.81-1.26 (m, 15H, 6CH$_2$, CH$_3$), 1.50 and 1.29 (2s, 6H, 2CH$_3$), 1.87 (m, 3H, CH$_3$); $^{13}$C-NMR (75 MHz, CDCl$_3$) δ 143.8 (C-1'), 128.9 and 128.0 (C-2' and C-3'), 127.3 (C-4'), 111.7 (C(CH$_3$)$_2$), 87.2 (CPh$_3$), 87.2 (H-2), 79.1 (H-2, H-4), 67.8 (H-5), 64.1 (H-6), 49.6, 35.9, 32.1, 29.6, 29.5, 29.4, 29.4, 26.5, 26.3, 23.7, 22.8 (CH$_2$), 27.3 and 25.8 (2CH$_3$), 14.3 (CH$_3$), 10.4 (CH$_3$).

Step 7: Synthesis of ((1S,2R,3S,4S,5R)-1-octhyl-2,3-diol-5,6-dihydroxyethyl pyrrolidine trifluoroacetate salt)

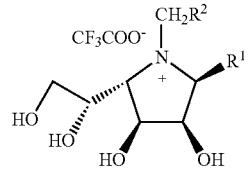

((1S,2R,3S,4S,5R)-1-Methyl-N-nonyl-2,3-isopropylidenedioxy-6-O-triphenylmethyl-5,6-dihydroxyethyl pyrrolidine acetate salt (0.85 g, 1.46 mmol) was dissolved in trifluoroacetic acid/water 1:1 (2 ml) at room temperature. The mixture was allowed to stand at room temperature overnight and then evaporated to dryness. Purification by flash chromatography (acetate/methanol 4:1) afforded ((1S,2R,3S,4S,5R)-1-octhyl-2,3-diol-5,6-dihydroxyethyl pyrrolidine trifluoroacetate salt (87%) as a colorless oil.
C$_{18}$F$_3$H$_{34}$NO$_6$, M=417.45; For C$_{16}$H$_{33}$NO$_4$ MS m/z 304.3 (M+H).

Example 4

Preparation of ((1S,2R,3S,4S,5S)-1-octyl-2,3-diol-5,6-dihydroxyethyl pyrrolidine)

Step 1: Synthesis of 6-O-tert-Butyldimethylsilyl-2,3-O-isopropylidene-L-gulonolactone

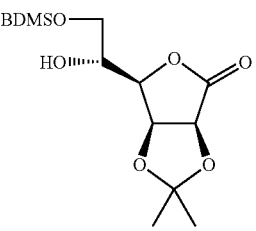

L-Gulono-1,4-lactone (Sigma Aldrich) was converted into the diacetonide with dimetoxypropane in the presence of catalytic amount of p-toluenesulfonic acid, the side chain isopropylidene protecting group was selectively hydrolysed to 2,3-O-isopropylidene-L-gulonolactone, see e.g. (a) Fleet G. W.; Ramsden N. G.; Witty D. R. *Tetrahedron Letters* 1988, 29(23), 2871. (b) Fleet G. W.; Ramsden N. G.; Witty D. R. *Tetrahedron* 1989, 45(1), 319. (c) Ogura H.; Takakashi H.; Itoh T. *J. Org. Chem.* 1972, 37, 72, all incorporated herein by reference in their entirety. A solution of tert-butyldimethylsilyl chloride (3.47 g, 23 mmoli, 1.2 eq) and imidazole (1.9 g, 28 moli, 1.45 eq) in dry DMF (40 ml) was added to a stirred solution of 2,3-O-isopropilidene-L-gulonolactone-1,4-lactone (4.2 g, 19 mmoli) in dry DMF (60 ml) at −10° C. under argon. The reaction mixture was then stirred at RT for 5 h, when TLC (ethyl acetate hexane 1:2) showed no starting material. The solvent was removed under reduced pressure and the residue dissolved in chloroform (15 ml), the chloroform solution was washed with water, dried (MgSO$_4$) and evaporated. Purification by flash chromatography (ethyl acetate/hexane 1:2) afforded 6-O-tert-butyldimethylsilyl-2,3-O-isopropylidene-L-gulonolactone (%) as colorless oil (lit 71%, colorless oil).

$^1$H-NMR (400 MHz, CDCl$_3$) δ
$^{13}$C-NMR (75 MHz, CDCl$_3$) δ

Step 2: Synthesis of 5-O-Methanesulfonyl-6-O-tert-butyldimethylsilyl-2,3-O-isopropylidene-L-gulonolactone

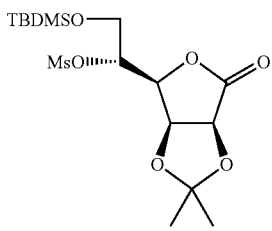 [SMILES: CC1(C)O[C@H]2[C@@H]([C@@H](CO[Si](C)(C)C(C)(C)C)OS(C)(=O)=O)OC(=O)[C@H]2O1]

6-O-tert-Butyldimethylsilyl-2,3-O-isopropylidene-L-gulonolactone (3 g, 9 mmoli, 1 eq) was dissolved in pyridine (6 ml) and methanesulfonylchloride (0.88 ml, 10 mmoli, 1.2 eq) was added to a stirred at 0° C. over 10 min. The mixture was kept at 0° C. for 1 h. 0.2 ml water was then added and the mixture was extracted with methylene chloride (15 ml). The extract was washed with HCl 10% (5 ml) and with aqueous NaHCO$_3$ (5 ml). The organic phase was dried (MgSO$_4$), filtered and evaporated under reduced pressure to yield 5-O-methanesulfonyl-6-O-tert-butyldimethylsilyl-2,3-O-isopropylidene-L-gulonolactone (90%) as a crystals, mp 113-114° C. C$_{16}$H$_{30}$O$_8$SSi, M=383.5: MS m/z (M+)

$^1$H-NMR (400 MHz, CDCl$_3$) δ
$^{13}$C-NMR (75 MHz, CDCl$_3$) δ

Step 3: Synthesis of 1-octyl-2,3-O-isopropylidene-5-O-methanesulfonyl-6-O-tert-butyldimethylsilyl-L-gulose

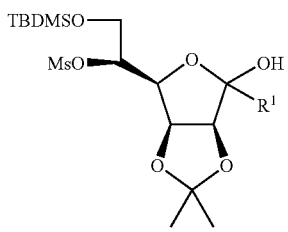

5-O-Methanesulfonyl-6-O-tert-butyldimethylsilyl-2,3-O-isopropylidene-L-gulono-1,4 lactone (1 eq) was dissolved in THF (160 ml) anhydrous under Ar. The solution was cooled to −68° C., maintaining the temperature between −50° C.~−40° C., the Grignard reagent (1.5 eq) was added with stirred over 20 min. The temperature was allowed to warm to 0° C. and the solution was stirred 2 h. After quenching with saturated aqueous NH$_4$Cl, the mixture was extracted with ethyl acetate. The combined extracts were washed with saturated aqueous NH$_4$Cl, dried over Na$_2$SO$_4$, and filtered. Evaporation of the filtrate under vacuo afforded 1-octyl-2,3-O-isopropylidene-5-O-methanesulfonyl-6-O-tert-butyldimethylsilyl-L-gulose (95%), colorless crystals, mp 76-78° C., as a stereoisomer mixture at the anomeric carbon atom. Ratio of isomers α:β~79:21. C$_{24}$H$_{48}$O$_8$SSi, M=524.78: MS m/z 547.1 (M+Na); $^1$H-NMR (400 MHz, CDCl$_3$) δ α: 4.79-4.72 (m, 2H, H-3, H-5), 4.48 (d, J$_{2,3}$=5.9 Hz, 1H, H-2), 4.37 (dd, J$_{4,5}$=8.9, Hz, J$_{4,3}$=3.7 Hz, H-4), 4.04-3.96 (m, 2H, H-6', H-6), 3.06 (s, 3H, CH$_3$SO$_2$), 1.87-1.64 (m, 2H, CH$_2$), 1.45 and 1.30 (2s, 6H, 2CH$_3$), 1.45-1.24 (m, 12H, 6CH$_2$), 0.90-0.86 (m, 12H, 4CH$_3$), 0.1 (s, 6H, 2CH$_3$); β: 4.31 (d, J$_{2,3}$=5.9 Hz, 1H, H-2), 3.88 (dd, J$_{4,5}$=8.5, Hz, J$_{4,3}$=3.5 Hz, H-4), 3.11 (s, 3H, CH$_3$SO$_2$), 1.54 and 1.36 (2s, 6H, 2CH$_3$); $^{13}$C-NMR (75 MHz, CDCl$_3$) δα: 112.9 (C-7), 106.9 (C-1), 85.4 (C-2), 83.6, 80.2 (C-3, C-5), 77.3 (C-4), 63.6 (C-6), 38.5 (CH$_3$SO$_2$), 35.5, 32.1, 29.9, 29.6, 29.4 (CH$_2$), 26.4 and 24.9 (2CH$_3$), 26.1 (3CH$_3$), 23.3, 22.8, (CH$_2$) 18.5 (C(CH$_3$)$_3$), 14.3 (CH$_3$), −5.4 (2CH$_3$); β: 113.5 (C-7), 104.1 (C-1), 83.7 and 79.7 (C-3, C-5), 82.1 (C-2), 74.9 (H-4), 63.8 (H-6), 38.7 (CH$_3$SO$_2$).

Step 4: Synthesis of ((2R,3S,4S,5S)-1-octyl-2,3-isopropylidenedioxy-6-O-tert-butyldimethylsilyl-5,6-hydroxyethyl-1-pyrroline

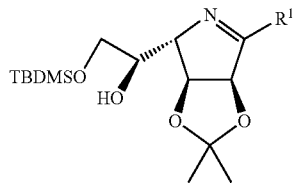

1-Octyl-2,3-O-isopropylidene-5-O-methanesulfonyl-6-O-tertbutyldimethylsilyl-L-gulose was dissolved in aq NH$_3$ and EtOH. The solution was allowed to stand 4 days at room temperature in a sealed flask. The solvent was removed under reduced pressure, and the residue was dissolved in methanol, dried over Na$_2$SO$_4$, and filtered. Evaporation of the filtrate under vacuo afforded the crude product which was purified by silica gel column chromatography, eluting with ethyl acetate, to afford ((2R,3S,4S,5S)-1-octyl-2,3-isopropylidenedioxy-6-O-tert-butyldimethylsilyl-5,6-hydroxyethyl-1-pyrroline as a colorless oil (25%). C$_{23}$H$_{45}$NO$_4$Si, M=427.7: MS m/z 428.5 (M+H). $^1$H-NMR (400 MHz, CDCl$_3$) δ 4.91 (s, J$_{3,2}$=5.5 Hz, 1H, H-3), 4.51 (s, J$_{2,3}$=5.5 Hz, 1H, H-3), 4.34 (s, 1H, H-4), 4.08 (m, 1H, H-5), 3.73 (dd, J$_{6',6}$=11.6 Hz, J$_{6',5}$=3.2 Hz, 1H, H-6'), 3.66 (dd, J$_{6,6'}$=11.6 Hz, J$_{6,5}$=5.2 Hz, 1H, H-6), 2.50-2.37 (m, 2H, CH$_2$), 1.71-1.26 (m, 18H, 8CH$_2$), 0.93-0.90 (m, 12H, 4CH$_3$), 0.1 (s, 6H, 2CH$_3$). $^{13}$C-NMR (75 MHz, CDCl$_3$) δ 179.1 (C=N), 111.6 (C-7), 86.2 (C-2), 81.1 (C-3), 79.9 (C-4), 72.8 (C-5), 65.3 (C-6), 32.1, 31.1, 29.9, 29.6, 29.5, 29.3, 27.1, 26.0, 22.8 (7CH$_2$, 2CH$_3$), 25.9 (3CH$_3$), 18.2 (C(CH$_3$)$_3$), 14.3 (CH$_3$), −4.2, −4.6 (2CH$_3$).

Step 5: Synthesis of ((1S,2R,3S,4S,5S)-1-octhyl-2,3-isopropylidenedioxy-6-O-tert-butyldimethylsilyl-5,6-dihydroxyethyl pyrrolidine acetate salt

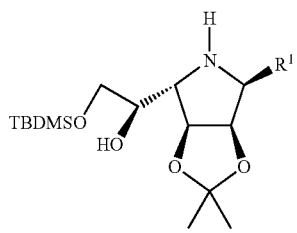

A solution of ((2R,3S,4S,5S)-1-octyl-2,3-isopropylidenedioxy-6-O-tert-butyldimethylsilyl-5,6-hydroxyethyl-1-pyrroline in acetic acid was shaken overnight under hydrogen in the presence of 10% palladium-carbon using 50 psi pressures. TLC (ethyl acetate: methanol, 4:1) showed complete reactions. The catalyst was removed by filtration through a celite pad and rinsed with acetic acid. Concentration in vacuo and purification of the residue by column chromatography (silica gel, elute with ethyl acetate: methanol, 4:1) afforded ((1S,2R,3S,4S,5S)-1-octhyl-2,3-isopropylidenedioxy-6-O-tert-butyldimethylsilyl-5,6-dihydroxyethyl pyrrolidine acetate salt as a colorless crystalline product, mp 87-89° C. (45%). C$_{23}$H$_{47}$NO$_4$Si, M=429.16: MS m/z 430.3 (M+H)$^+$.
$^1$H-NMR (400 MHz, CDCl$_3$) δ
$^{13}$C-NMR (75 MHz, CDCl$_3$) δ

Step 6: Synthesis of ((1S,2R,3S,4S,5S)-1-octyl-2,3-diol-5,6-dihydroxyethyl pyrrolidine

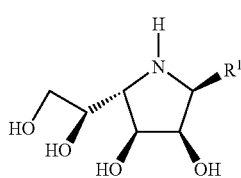

((1S,2R,3S,4S,5S)-1-octhyl-2,3-isopropylidenedioxy-6-O-tert-butyldimethylsilyl-5,6-dihydroxyethyl pyrrolidine acetate salt was dissolved in trifluoroacetic acid/water 1:1 (2 ml) at room temperature. The mixture was allowed to stand at room temperature overnight and then evaporated to dryness. Pyrrolidines trifluoroacetate salt were dissolved in aqueous methanol (1:1) and treated with Amberlyst A 21 base resin until the solution had pH 7. The solvent was removed under reduced pressure. Purification by flash chromatography (ethyl acetate/methanol 4:1) afforded ((1S,2R,3S,4S,5S)-1-octyl-2,3-diol-5,6-dihydroxyethyl pyrrolidine (94%) as a colorless oil. C$_{14}$H$_{29}$NO$_4$, M=275.39; MS m/z 276.3 (M+H);
$^1$H-NMR (400 MHz, CD$_3$OD) δ 4.1 (dd, J$_{3,4}$=8.3 Hz; J$_{3,2}$=4.0 Hz, 1H, H-3), 3.83 (dd, J$_{2,3}$=4.0 Hz, J$_{2,1}$=3.0 Hz, 1H, H-2), 3.61 (m, 1H, H-5), 3.59-3.51 (m, 2H, H-6', H-6), 1.45-1.43 (m, 2H, CH$_2$), 1.29-1.27 (m, H, CH$_2$), 0.87 (t, J=6.5 Hz, 3H, CH$_3$); $^{13}$C-NMR (75 MHz, CD$_3$OD) δ 76.2 (C-3), 74.3 (C-2), 73.1 (C-5), 65.9 (C-6), 63.8 (C-4), 61.6 (C-1), 33.2, 31.2, 31.1, 30.9, 30.6, 28.0, 23.9 (7CH$_2$), 14.6 (CH$_3$).

Example 5

Antiviral Activity of Iminocyclitols

The antiviral activity of selected iminocyclitols of the present invention was evaluated in the bovine viral diarrhoea virus assay (BVDV), see e.g. Mehta, A.; Ouzounov, S.; Jordan, R.; Simsek, E.; Lu, X.; Moriarty, R. M.; Jacob, G.; Dwek, R. A.; Block, T. M. *Antivir. Chem. Chemother.* 2002, 13(5), 299. The pair of compounds

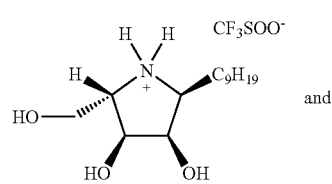

44

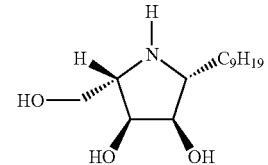

45 having only the C$_1$ epimeric C$_9$H$_{19}$ groups and no alkyl groups on nitrogen both possess IC$_{50}$ of 1.5 µM and IC$_{90}$ of 2.2 µM, respectively. These values are superior to N-n-butyl DNJ (IC$_{50}$=125 µM) and N-n-nonyl DNJ (IC$_{50}$=10 µM), see e.g. a) Block, T. M.; Lu, X.; Platt, F. M.; Foster, G. R.; Gerlich, W. H.; Blumberg, B. S.; Dwek, R. A. *Proc. Natl. Acad. Sci. U.S.A.* 1994, 91(6), 2235; b) Branza-Nichita, N.; Durantel, D.; Carrouée-Durantel, S.; Dwek, R. A.; Zitzmann, N. *J. Virol.* 2001, 75(8), 3527; c) Durantel, D.; Branza-Nichita, N.; Carrouée-Durantel, S.; Butters, T. D.; Dwek, R. A.; Zitzmann, N. *J. Virol.* 2001, 75(19), 8987, all incorporated herein by reference in their entirety. The N-alkyl-C-alkyl analogs

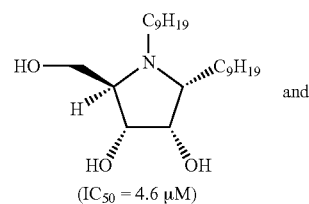

46

(IC$_{50}$ = 4.6 µM)

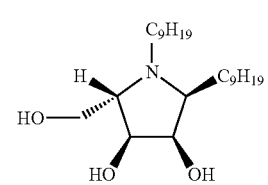

47

(IC$_{50}$=8.2 µM) in the D-ribo and L-ribitol series, respectively, and were less active relative to the N-desalkyl (NH) 44 and 45. In the L-xylitol series the opposite behavior was observed. The viral activity of compounds

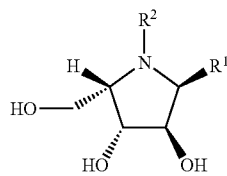

with a) $R^2$=H and $R^1$=$C_9H_{19}$; b) $R^2$=$C_6H_{13}$ and $R^1$=$C_8H_{17}$; c) $R^2$=$C_8H_{17}$ and $R^1$=$C_8H_{17}$; d) $R^2$=$R^1$=$C_8H_{17}$ has been studied. Compounds, 48b-d (48b: $IC_{50}$=0.37 μM, 48c: $IC_{50}$=0.4 μM, 48d: $IC_{50}$=1 μM) are not only more active than 48a ($IC_{50}$=1 μM), but show very impressive antiviral activity relative to all 1,4-iminocyclitols reported to date. These analogs can be considered good leads and point to the value of the combinatorial application of the exo-imino to endo-iminocyclitol process.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All the publications, patent applications and patents cited in this specification are incorporated herein by reference in their entirety.

What is claimed is:

1. A method of synthesizing a stereochemically defined iminocyclitol comprising
reacting a cyclic sugar containing an intraring oxygen with a reagent comprising $NH_3$, wherein said reacting results in replacing the intraring oxygen in the cyclic sugar by an intraring nitrogen to form an iminocyclitol, wherein said iminocyclitol has a defined stereochemical configuration different from a stereochemical configuration of the cyclic sugar, wherein a ring size of said iminocyclitol is the same as a ring size of said cyclic sugar and wherein said nitrogen forms an imine group —N= in said iminocyclitol, wherein the cyclic sugar is an aldopentose in a 4-deoxy 1,4 furanose form, an aldohexose in a 4-deoxy 1,4 furanose form or an aldohexose in a 2,5-dideoxy pyranose form and wherein the cyclic sugar is substituted at the C1 position by $R^1$, wherein $R^1$ is an alkyl group comprising from 1 to 20 carbon atoms.

2. The method of claim 1, further comprising reacting a protected lactone compound with a Grignard reagent $R^1MgX$ to form the cyclic sugar, wherein a stereochemical configuration of the protected lactone compound is the same as the stereochemical configuration of the cyclic sugar.

3. The method of claim 2, further comprising protecting hydroxyl groups of an unprotected lactone compound to form the protected lactone compound, wherein a stereochemical configuration of the unprotected lactone compound is the same as the stereochemical configuration of the protected lactone compound.

4. The method of claim 3, wherein the unprotected lactone compound is an aldopentose or an aldohexose in a 4-deoxy 1,4 furanose form and wherein said protecting hydroxyl groups comprises protecting a hydroxyl group on the C5 atom of the unprotected lactone compound with methanesulfonate, tosylate or triflate protective group.

5. The method of claim 3, wherein the unprotected lactone compound is an aldohexose in a 4-deoxy 1,4 furanose form and wherein said protecting hydroxyl groups comprises protecting a hydroxyl group on the C6 atom of the unprotected lactone compound with a trityl or t-butyldimethylsiloxy group.

6. The method of claim 3, wherein the unprotected lactone compound is an aldohexose in a 2,5-dideoxy pyranose form and wherein said protecting hydroxyl groups comprises protecting a hydroxyl group on the C6 atom of the unprotected lactone compound with a methanesulfonate protective group.

7. The method of claim 3, wherein the unprotected lactone compound is an aldopentose or an aldohexose in a 4-deoxy 1,4 furanose and wherein said protecting hydroxyl groups comprises protecting a hydroxyl group on the C2 atom and a hydroxyl group on the C3 atom by an isopropylindene.

8. The method of claim 3, wherein the unprotected lactone compound is an aldohexose in a 2,5-dideoxy pyranose form and wherein said protecting hydroxyl groups comprises protecting a hydroxyl group on the C3 atom and a hydroxyl group on the C4 atom by an isopropylindene.

9. The method of claim 3, wherein the unprotected lactone compound is an aldopentose or an aldohexose in a 4-deoxy 1,4 furanose, wherein said protecting hydroxyl groups comprises protecting a hydroxyl group on the C2 atom and a hydroxyl group on the C3 atom by benzyl, t-butyldimethylsiloxy or triphenylmethyl groups.

10. The method of claim 3, wherein the unprotected lactone compound is an aldohexose in a 2,5-dideoxy pyranose form and wherein said protecting hydroxyl groups comprises protecting a hydroxyl group on the C3 atom and a hydroxyl group on the C4 atom by benzyl, t-butyldimethylsiloxy or triphenylmethyl groups.

11. The method of claim 3, further comprising hydrogenating the iminocyclitol to form a hydrogenated iminocyclitol, wherein a stereochemical configuration of the hydrogenated iminocyclitol is the same as the stereochemical configuration of the iminocyclitol.

12. The method of claim 11, wherein hydrogenating the iminocyclitol is carried out in the presence of a catalyst.

13. The method of claim 12, wherein the catalyst comprises Pd/C and acetic acid.

14. The method of claim 11, further comprising alkylating the hydrogenated iminocyclitol to form a N-alkyl-C-alkyl iminocyclitol, wherein a stereochemical configuration of the N-alkyl-C-alkyl iminocyclitol is the same as the stereochemical configuration of the hydrogenated iminocyclitol.

15. The method of claim 14, wherein said alkylating the hydrogenated iminocyclitol comprises (a) reacting the hydrogenated iminocyclitol with an aldehyde $R^2CHO$ and the N atom of the N-alkyl-C-alkyl iminocyclitol has a substituent group $R^2CH_2$, and wherein $R^2$ is hydrogen or an alkyl group comprising from 1 to 20 carbon atoms, and (b) deprotecting C2 and C3 hydroxyl groups of the N-alkyl-C-alkyl iminocyclitol.

16. The method of claim 15, wherein the hydrogenating the iminocyclitol, the reacting the hydrogenated iminocyclitol with an aldehyde and the deprotecting C2 and C3 hydroxyl groups of the N-alkyl-C-alkyl iminocyclitol are carried out simultaneously.

17. The method of claim 2, wherein the cyclic sugar is an aldopentose in a 4-deoxy-1,4-furanose form.

18. The method of claim 2, wherein the cyclic sugar is an aldohexose in a 4-deoxy-1,4-furanose form.

19. The method of claim 2, wherein the cyclic sugar is an aldohexose in a 2,5-dideoxy-pyranose form.

20. The method of claim 4, wherein the unprotected lactone is an aldopentose in a 4-deoxy-1,4-furanose form.

21. The method of claim 4, wherein the unprotected lactone is an aldohexose in a 4-deoxy-1,4-furanose form.

22. The method of claim 7, wherein the unprotected lactone is an aldopentose in a 4-deoxy-1,4-furanose form.

23. The method of claim 7, wherein the unprotected lactone is an aldohexose in a 4-deoxy-1,4-furanose form.

24. The method of claim 9, wherein the unprotected lactone is an aldopentose in a 4-deoxy-1,4-furanose form.

25. The method of claim 9, wherein the unprotected lactone is an aldohexose in a 4-deoxy-1,4-furanose form.

26. The method of claim 15, wherein the N-alkyl-C-alkyl iminocyclitol has the following formula:

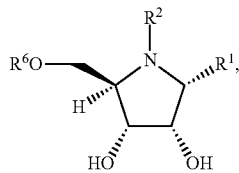

wherein $R^1$ is an alkyl group comprising 1 to 20 carbon atoms, $R^2$ is an alkyl group comprising 1 to 20 carbon atoms and $R^6$ is hydrogen.

27. The method of claim 15, wherein the N-alkyl-C-alkyl iminocyclitol has the following formula:

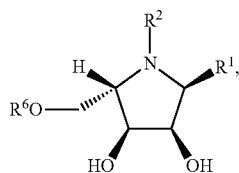

wherein $R^1$ is an alkyl group comprising 1 to 20 carbon atoms, $R^2$ is an alkyl group comprising 1 to 20 carbon atoms and $R^6$ is hydrogen.

28. The method of claim 15, wherein the N-alkyl-C-alkyl iminocyclitol has the following formula:

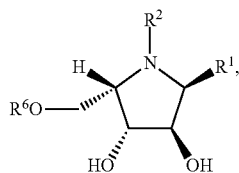

wherein $R^1$ is an alkyl group comprising 1 to 20 carbon atoms, $R^2$ is an alkyl group comprising 1 to 20 carbon atoms and $R^6$ is hydrogen.

29. A method of synthesizing a stereochemically defined iminocyclitol comprising:
   (a) protecting hydroxyl groups of an unprotected lactone compound to form the protected lactone compound, wherein a stereochemical configuration of the unprotected lactone compound is the same as the stereochemical configuration of the protected lactone compound;
   (b) reacting the protected lactone compound with a Grignard reagent $R^1MgX$ to form a cyclic sugar containing an intraring oxygen, wherein a stereochemical configuration of the protected lactone compound is the same as the stereochemical configuration of the cyclic sugar, wherein the cyclic sugar is an aldopentose in a 4-deoxy 1,4 furanose form, an aldohexose in a 4-deoxy 1,4 furanose form or an aldohexose in a 2,5-dideoxy pyranose form and wherein the cyclic sugar is substituted at the C1 position by $R^1$, wherein $R^1$ is an alkyl group comprising from 1 to 20 carbon atoms;
   (c) reacting the cyclic sugar with a reagent comprising $NH_3$, wherein said reacting results in replacing the intraring oxygen in the cyclic sugar by an intraring nitrogen to form an iminocyclitol, wherein said iminocyclitol has a defined stereochemical configuration different from a stereochemical configuration of the cyclic sugar, wherein a ring size of said iminocyclitol is the same as a ring size of said cyclic sugar and wherein said nitrogen forms an imine group —N= in said iminocyclitol; and
   (d) hydrogenating the iminocyclitol to form a hydrogenated iminocyclitol, wherein a stereochemical configuration of the hydrogenated iminocyclitol is the same as the stereochemical configuration of the iminocyclitol.

30. The method of claim 29, wherein the unprotected lactone is an aldopentose in a 4-deoxy-1,4-furanose form.

31. The method of claim 29, wherein the unprotected lactone is an aldohexose in a 4-deoxy-1,4-furanose form.

32. The method of claim 29, wherein the unprotected lactone is an aldohexose in a 2,5-dideoxy-pyranose form.

33. The method of claim 29, further comprising alkylating the hydrogenated iminocyclitol to form a N-alkyl-C-alkyl iminocyclitol, wherein a stereochemical configuration of the N-alkyl-C-alkyl iminocyclitol is the same as the stereochemical configuration of the hydrogenated iminocyclitol.

34. The method of claim 33, wherein the N-alkyl-C-alkyl iminocyclitol has the following formula:

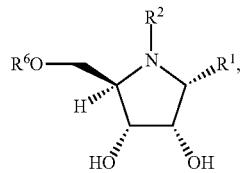

wherein $R^1$ is an alkyl group comprising 1 to 20 carbon atoms, $R^2$ is an alkyl group comprising 1 to 20 carbon atoms and $R^6$ is hydrogen.

35. The method of claim 33, wherein the N-alkyl-C-alkyl iminocyclitol has the following formula:

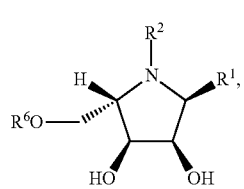

wherein $R^1$ is an alkyl group comprising 1 to 20 carbon atoms, $R^2$ is an alkyl group comprising 1 to 20 carbon atoms and $R^6$ is hydrogen.

36. The method of claim 33, wherein the N-alkyl-C-alkyl iminocyclitol has the following formula:
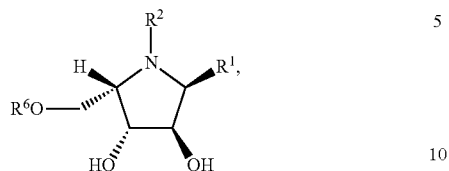
wherein $R^1$ is an alkyl group comprising 1 to 20 atoms, $R^2$ is an alkyl group comprising 1 to 20 carbon atoms and $R^6$ is hydrogen.
* * * * *